(12) United States Patent
Soane et al.

(10) Patent No.: US 11,357,857 B2
(45) Date of Patent: Jun. 14, 2022

(54) EXCIPIENT COMPOUNDS FOR PROTEIN PROCESSING

(71) Applicant: COMERA LIFE SCIENCES, INC., Woburn, MA (US)

(72) Inventors: David S. Soane, Palm Beach, FL (US); Philip Wuthrich, Watertown, MA (US); Robert P. Mahoney, Newbury, MA (US); Mark Moody, Concord, MA (US); Daniel G. Greene, Belmont, MA (US); Neil L. Schauer, Milford, MA (US)

(73) Assignee: Comera Life Sciences, Inc., Woburn, MA (US)

( * ) Notice: Subject to any disclaimer, the term of this patent is extended or adjusted under 35 U.S.C. 154(b) by 0 days.

(21) Appl. No.: 15/896,374

(22) Filed: Feb. 14, 2018

(65) Prior Publication Data
US 2019/0054175 A1 Feb. 21, 2019

Related U.S. Application Data

(63) Continuation-in-part of application No. 15/331,197, filed on Oct. 21, 2016, now Pat. No. 10,478,498, which is a continuation-in-part of application No. 14/966,549, filed on Dec. 11, 2015, now Pat. No. 9,605,051, which is a continuation-in-part of application No. 14/744,847, filed on Jun. 19, 2015, now abandoned.

(Continued)

(51) Int. Cl.
| | |
|---|---|
| *A61K 39/395* | (2006.01) |
| *A61K 47/22* | (2006.01) |
| *A61K 47/18* | (2017.01) |
| *A61K 9/00* | (2006.01) |
| *A61K 47/12* | (2006.01) |
| *A61K 47/60* | (2017.01) |
| *A61K 47/24* | (2006.01) |
| *A61K 47/20* | (2006.01) |
| *C07K 16/00* | (2006.01) |
| *A61K 47/42* | (2017.01) |
| *A61K 38/38* | (2006.01) |
| *A61K 38/47* | (2006.01) |
| *C12N 9/36* | (2006.01) |
| *C12N 9/96* | (2006.01) |
| *A61K 38/19* | (2006.01) |
| *A61K 38/17* | (2006.01) |
| *A61K 47/02* | (2006.01) |
| *A61K 38/18* | (2006.01) |
| *C07K 16/22* | (2006.01) |
| *C07K 16/32* | (2006.01) |

(52) U.S. Cl.
CPC ............ *A61K 47/22* (2013.01); *A61K 9/0019* (2013.01); *A61K 38/1793* (2013.01); *A61K 38/1816* (2013.01); *A61K 38/193* (2013.01); *A61K 38/385* (2013.01); *A61K 38/47* (2013.01); *A61K 39/395* (2013.01); *A61K 39/39591* (2013.01); *A61K 47/02* (2013.01); *A61K 47/12* (2013.01); *A61K 47/18* (2013.01); *A61K 47/183* (2013.01); *A61K 47/20* (2013.01); *A61K 47/24* (2013.01); *A61K 47/42* (2013.01); *A61K 47/60* (2017.08); *C07K 16/00* (2013.01); *C07K 16/22* (2013.01); *C07K 16/32* (2013.01); *C12N 9/2462* (2013.01); *C12N 9/96* (2013.01); *C12Y 302/01017* (2013.01)

(58) Field of Classification Search
None
See application file for complete search history.

(56) References Cited

U.S. PATENT DOCUMENTS

| | | | |
|---|---|---|---|
| 4,548,827 | A | 10/1985 | Katz et al. |
| 4,722,844 | A | 2/1988 | Ozawa et al. |

(Continued)

FOREIGN PATENT DOCUMENTS

| | | |
|---|---|---|
| CA | 3002373 A1 | 4/2017 |
| CN | 101378773 A | 3/2009 |

(Continued)

OTHER PUBLICATIONS

Stone, E. M., et al., "Replacing Mn2+ with Co2+ in Human Arginase I Enhances Cytotoxicity toward L-Arginine Auxotrophic Cancer Cell Lines," ACS Chemical Biology, 5(3): 333-342 (2010).
Becker, D. E., et al., "Local Anesthetics: Review of Pharmacological Considerations," Anesth Prog., 59: 90-102 (2012).
Becker, D. E., et al., "Essentials of Local Anesthetic Pharmacology," Anesth Prog, 53: 98-109 (2006).
Stone, E., et al., "Strategies for optimizing the serum persistence of engineered human arginase I for cancer therapy," J. of Controlled Release, 158: 171-179 (2012).

(Continued)

*Primary Examiner* — Yunsoo Kim
(74) *Attorney, Agent, or Firm* — Elmore Patent Law Group, P.C.; Mahreen Chaudhry Hoda; Carolyn S. Elmore

(57) ABSTRACT

Disclosed herein are methods for improving a parameter of a protein-related process comprising providing a viscosity-reducing excipient compound selected from the group consisting of hindered amines, anionic aromatics, functionalized amino acids, oligopeptides, short-chain organic acids, and low molecular weight aliphatic polyacids, and adding a viscosity-reducing amount of the viscosity-reducing excipient compound to a carrier solution for the protein-related process, wherein the carrier solution contains a protein of interest, and carrier solutions comprising a liquid medium in which is dissolved a protein of interest, and a viscosity-reducing excipient, wherein the viscosity of the carrier solution has a lower viscosity that that of a control solution that is substantially similar to the carrier solution except for the presence of the viscosity-reducing excipient.

21 Claims, 2 Drawing Sheets

Related U.S. Application Data

(60) Provisional application No. 62/459,893, filed on Feb. 16, 2017, provisional application No. 62/014,784, filed on Jun. 20, 2014, provisional application No. 62/083,623, filed on Nov. 24, 2014, provisional application No. 62/136,763, filed on Mar. 23, 2015, provisional application No. 62/245,513, filed on Oct. 23, 2015.

(56) References Cited

U.S. PATENT DOCUMENTS

| | | | |
|---|---|---|---|
| 5,063,246 | A | 11/1991 | Imai et al. |
| 5,164,214 | A | 11/1992 | Wild |
| 5,262,296 | A | 11/1993 | Ogawa et al. |
| 5,608,038 | A | 3/1997 | Eibl et al. |
| 5,849,700 | A | 12/1998 | Sorensen et al. |
| 5,871,736 | A | 2/1999 | Bruegger et al. |
| 5,900,416 | A | 5/1999 | Markson |
| 6,013,773 | A | 1/2000 | Kobayashi et al. |
| 6,171,586 | B1 | 1/2001 | Lam et al. |
| 6,267,958 | B1 | 7/2001 | Andya et al. |
| 6,525,102 | B1 | 2/2003 | Chen et al. |
| 6,685,940 | B2 | 2/2004 | Andya et al. |
| 6,875,432 | B2 | 4/2005 | Liu et al. |
| 7,390,786 | B2 | 6/2008 | Warne et al. |
| 7,666,413 | B2 | 2/2010 | Liu et al. |
| 7,758,860 | B2 | 7/2010 | Warne et al. |
| 7,947,649 | B2 | 5/2011 | Su et al. |
| 7,956,028 | B2 | 6/2011 | Garigapati et al. |
| 7,964,561 | B2 | 6/2011 | Garigapati et al. |
| 8,013,022 | B2 | 9/2011 | DeAngelo et al. |
| 8,142,776 | B2 | 3/2012 | Liu et al. |
| 8,318,161 | B2 | 11/2012 | Esue |
| 8,383,114 | B2 | 2/2013 | Sloey et al. |
| 8,420,081 | B2 | 4/2013 | Fraunhofer et al. |
| 8,440,184 | B2 | 5/2013 | Georgiou et al. |
| 8,476,239 | B2 | 7/2013 | Dali et al. |
| 8,512,754 | B2 | 8/2013 | Needham |
| 8,568,720 | B2 | 10/2013 | Morichika et al. |
| 8,613,919 | B1 | 12/2013 | Ma et al. |
| 8,617,568 | B2 | 12/2013 | Jung et al. |
| 8,679,479 | B2 | 3/2014 | Georgiou et al. |
| 8,703,126 | B2 | 4/2014 | Liu et al. |
| 8,715,652 | B2 | 5/2014 | Bolli et al. |
| 8,961,964 | B2 | 2/2015 | Liu et al. |
| 9,339,545 | B2 | 5/2016 | Prestrelski et al. |
| 9,605,051 | B2 | 3/2017 | Soane et al. |
| 9,649,364 | B2 | 5/2017 | Prestrelski et al. |
| 9,867,881 | B2 | 1/2018 | Soane et al. |
| 9,943,601 | B2 | 4/2018 | Manning et al. |
| 10,000,562 | B2 | 6/2018 | Deshmukh et al. |
| 10,206,924 | B2 | 2/2019 | Whitehead et al. |
| 10,279,048 | B2 | 5/2019 | Soane et al. |
| 10,478,498 | B2 | 11/2019 | Soane et al. |
| 10,646,569 | B2 | 5/2020 | Shenoy |
| 2002/0045571 | A1 | 4/2002 | Liu et al. |
| 2003/0092607 | A1 | 5/2003 | Carpenter et al. |
| 2003/0113316 | A1 | 6/2003 | Kaisheva et al. |
| 2003/0138417 | A1 | 7/2003 | Kaisheva et al. |
| 2003/0202972 | A1 | 10/2003 | Andya et al. |
| 2004/0081702 | A1 | 4/2004 | Kim |
| 2004/0191243 | A1 | 9/2004 | Chen et al. |
| 2004/0197324 | A1 | 10/2004 | Liu et al. |
| 2005/0158303 | A1 | 7/2005 | Liu et al. |
| 2005/0175603 | A1 | 8/2005 | Liu et al. |
| 2006/0182740 | A1* | 8/2006 | Yang ............... A61K 47/183 |
| | | | 424/133.1 |
| 2006/0216377 | A1 | 9/2006 | Milton et al. |
| 2007/0053900 | A1 | 3/2007 | Liu et al. |
| 2007/0086995 | A1 | 4/2007 | Liu et al. |
| 2007/0116700 | A1 | 5/2007 | Liu et al. |
| 2008/0071063 | A1 | 3/2008 | Allan et al. |
| 2009/0035275 | A1 | 2/2009 | Pickering et al. |
| 2009/0280129 | A1 | 11/2009 | Liu et al. |
| 2009/0291062 | A1* | 11/2009 | Fraunhofer ......... A61K 9/0019 |
| | | | 424/85.5 |
| 2010/0239567 | A1 | 9/2010 | Esue |
| 2010/0297106 | A1 | 11/2010 | Sloey et al. |
| 2011/0046052 | A1 | 2/2011 | Yang |
| 2011/0066111 | A1 | 3/2011 | Teschner et al. |
| 2011/0106044 | A1 | 5/2011 | Trotter et al. |
| 2011/0112029 | A1 | 5/2011 | Nielsen et al. |
| 2012/0076783 | A1 | 3/2012 | Liu et al. |
| 2012/0082715 | A1 | 4/2012 | Needham |
| 2013/0058958 | A1 | 3/2013 | Bowen et al. |
| 2013/0071411 | A1 | 3/2013 | Boudreault et al. |
| 2013/0102760 | A1 | 4/2013 | Bolli et al. |
| 2013/0149335 | A1 | 6/2013 | Jezek et al. |
| 2013/0171128 | A1 | 7/2013 | Huang et al. |
| 2013/0216525 | A1 | 8/2013 | Chen |
| 2013/0309226 | A1 | 11/2013 | Armstrong et al. |
| 2014/0072559 | A1 | 3/2014 | Soula |
| 2014/0255423 | A1 | 9/2014 | Hickman et al. |
| 2014/0378655 | A1 | 12/2014 | Anderson |
| 2015/0007187 | A1 | 1/2015 | Shows |
| 2015/0044198 | A1 | 2/2015 | Liu et al. |
| 2015/0071879 | A1 | 3/2015 | Jezek |
| 2015/0071920 | A1 | 3/2015 | Larson et al. |
| 2015/0071921 | A1 | 3/2015 | Larson et al. |
| 2015/0071922 | A1 | 3/2015 | Larson et al. |
| 2015/0071925 | A1 | 3/2015 | Larson et al. |
| 2015/0225485 | A1 | 8/2015 | Liu et al. |
| 2016/0010063 | A1 | 1/2016 | Selvitelli et al. |
| 2016/0271253 | A1 | 9/2016 | Chang |
| 2017/0232103 | A1 | 8/2017 | Soane et al. |
| 2020/0316196 | A1 | 10/2020 | Soane et al. |

FOREIGN PATENT DOCUMENTS

| | | |
|---|---|---|
| CN | 101442915 A | 5/2009 |
| CN | 102946903 A | 2/2013 |
| JP | 2012170366 A | 9/2012 |
| JP | 2015522019 A | 8/2015 |
| WO | 97/27750 A1 | 8/1997 |
| WO | 2004/037018 A1 | 5/2004 |
| WO | 2004/091658 A1 | 10/2004 |
| WO | 2006/119054 A2 | 11/2006 |
| WO | 2011/109415 A2 | 9/2011 |
| WO | 2011/139718 A1 | 11/2011 |
| WO | 2014037680 A1 | 3/2014 |
| WO | 20150038818 A1 | 3/2015 |
| WO | 2015/196091 A1 | 12/2015 |
| WO | 2016/054259 A1 | 4/2016 |

OTHER PUBLICATIONS

Glazer, E., S., et al., "Bioengineered Human Arginase I with Enhanced Activity and Stability Controls Hepatocellular and Pancreatic Carcinoma Xenografts," Translational Oncology, 4(3): 138-146 (2011).

Antihistamine, retrieved from the internet on Jun. 10, 2015. <<http://faculty.weber.edu/ewalker/Medicinal_Chemistry/topics/Antihistam_local_anesth/antihista.htm>>. pp. 1-8.

Shi, S., et al., "Method qualification and application of diffusion interaction parameter and virial coefficient," Intl. J. of Biological Macromolecules, 62: 487-493 (2013).

Local Anesthetics handout, retrieved from the Internet on Oct. 15, 2015. <<http://www.medbox.org/surgery-anaesthesia/local-anesthesia-handout/preview?q=>>. International federation of nurse anesthetics, (2014).

"Aeglea Biotherapeutics Raises $44 Million in Series B Financing," Mar. 23, 2015 Press Release, retrieved from the internet <<http://ir.aegleabio.com/phoenix.zhtml?c=254096&p=irol-newsArticle&ID=2069753>>.

Weight, A. K., "Enhancing pharmaceutical formulations to improve efficacy and delivery of drug molecules," paper submitted at the Massachusetts Institute of Technology Jun. 2013, pp. 1-93.

Tomar, D. S., et al., "Molecular basis of high viscosity in concentrated antibody solutions: Strategies for high concentration drug product development," MABS, 8(2): 216-228 (2016).

(56) References Cited

OTHER PUBLICATIONS

Connolly, B. D., et al., "Weak Interactions Govern the Viscosity of Concentrated Antibody Solutions High~Throughput Analysis Using the Diffusion Interaction Parameter," Biophysical Journal, 103: 69-78 (2012).
Du, W., et al., "Hydrophobic Salts Markedly Diminish Viscosity of Concentrated Protein Solutions," Biotechnol. Bioeng. 2011;108: 632-636.
Guo, Z., et al., "Structure-Activity Relationship for Hydrophobic Salts as Viscosity-Lowering Excipients for Concentrated Solutions of Monoclonal Antibodies," Pharm Res (2012) 29:3102-3109.
"GNPD-Coffee Drink", pp. 1-2, retrieved from the internet: URL: http://www.gnpd.com/sinatra/recordpage/10245855/from_search/flEWaYhnVb/?page=1 [retrieved on Nov. 9, 2011].
Hung, J. J., "High Concentration Tangential Flow Ultrafiltration of Stable Monoclonal Antibody Solutions with Low Viscosities," Manuscript available via Elsevier.com, 2016.
Davidson, et al., "Effect of Sucrose/Raffinose Mass Ratios on the Stability of Co-Lyophilized Protein During Storage Above the Tg," Pharmaceutical Research, 18: 474-479 (2001).
Liu, J. et al., "Reversible self-association increases the viscosity of a concentrated monoclonal antibody in aqueous solution", J. Pharm. Sci., 94(9), Sep. 30, 2005, 1928-1940.
Yadav, S. et al., "Specific interactions in high concentration antibody solutions resulting high viscosity", J. Pharm. Sci., 99(3), Mar. 31, 2010, 1152-1158.
Xu, Shuyun et al., Clinical Pharmacology (vol. Two), published in Hefei by Anhui Science & Technology Press, Edition 1, pp. 711-712, date of publication: Jul. 31, 1981.
Chapter 1, Section II(F) of book titled "Caffeine" CRC press 1998, edited by Gene Spiller, ISBN 0-8493-2647-8.
http://www.inchem.org/documents/icsc/lcsc/eics0405.htm. Retrieved from the internet on Apr. 8, 2021.
https://pubchem.ncbi.nlm.nih.gov/compound/Caffeine; pp. 1-211. Retrieved from the internet on Apr. 8, 2021.

\* cited by examiner

EXCIPIENT COMPOUNDS FOR PROTEIN PROCESSING

RELATED APPLICATIONS

This application claims the benefit of U.S. Provisional Application No. 62/459,893 filed Feb. 16, 2017; this application is also a continuation-in-part of U.S. application Ser. No. 15/331,197 filed Oct. 21, 2016, which is a continuation-in-part of U.S. application Ser. No. 14/966,549 filed Dec. 11, 2015 (now U.S. Pat. No. 9,605,051), which is a continuation of U.S. application Ser. No. 14/744,847 filed Jun. 19, 2015 which claims the benefit of U.S. Provisional Application No. 62/014,784 filed Jun. 20, 2014, U.S. Provisional Application No. 62/083,623, filed Nov. 24, 2014, and U.S. Provisional Application Ser. No. 62/136,763 filed Mar. 23, 2015; U.S. application Ser. No. 14/966,549 also claims the benefit of U.S. Provisional Application No. 62/245,513, filed Oct. 23, 2015; U.S. application Ser. No. 15/331,197 also claims the benefit of U.S. Provisional Application No. 62/245,513, filed Oct. 23, 2015. The entire contents of the each of the above applications are incorporated by reference herein.

FIELD OF APPLICATION

This application relates generally to formulations for delivering and processing biopolymers.

BACKGROUND

Biopolymers may be used for therapeutic or non-therapeutic purposes. Biopolymer-based therapeutics, such as antibody or enzyme formulations, are widely used in treating disease. Non-therapeutic biopolymers, such as enzymes, peptides, and structural proteins, have utility in non-therapeutic applications such as household, nutrition, commercial, and industrial uses.

Biopolymers used in therapeutic applications must be formulated to permit their introduction into the body for treatment of disease. For example, it is advantageous to deliver antibody and protein/peptide biopolymer formulations by subcutaneous (SC) or intramuscular (IM) routes under certain circumstances, instead of administering these formulations by intravenous (IV) injections. In order to achieve better patient compliance and comfort with SC or IM injection though, the liquid volume in the syringe is typically limited to 2 to 3 ccs and the viscosity of the formulation is typically lower than about 20 centipoise (cP) so that the formulation can be delivered using conventional medical devices and small-bore needles. These delivery parameters do not always fit well with the dosage requirements for the formulations being delivered.

Antibodies, for example, may need to be delivered at high dose levels to exert their intended therapeutic effect. Using a restricted liquid volume to deliver a high dose level of an antibody formulation can require a high concentration of the antibody in the delivery vehicle, sometimes exceeding a level of 150 mg/mL. At this dosage level, the viscosity-versus-concentration plots of protein solutions lie beyond their linear-nonlinear transition, such that the viscosity of the formulation rises dramatically with increasing concentration. Increased viscosity, however, is not compatible with standard SC or IM delivery systems. The solutions of biopolymer-based therapeutics are also prone to stability problems, such as precipitation, hazing, opalescence, denaturing, and gel formation, reversible or irreversible aggregation. The stability problems limit the shelf life of the solutions or require special handling.

One approach to producing protein formulations for injection is to transform the therapeutic protein solution into a powder that can be reconstituted to form a suspension suitable for SC or IM delivery. Lyophilization is a standard technique to produce protein powders. Freeze-drying, spray drying and even precipitation followed by super-critical-fluid extraction have been used to generate protein powders for subsequent reconstitution. Powdered suspensions are low in viscosity before re-dissolution (compared to solutions at the same overall dose) and thus may be suitable for SC or IM injection, provided the particles are sufficiently small to fit through the needle. However, protein crystals that are present in the powder have the inherent risk of triggering immune response. The uncertain protein stability/activity following re-dissolution poses further concerns. There remains a need in the art for techniques to produce low viscosity protein formulations for therapeutic purposes while avoiding the limitations introduced by protein powder suspensions.

In addition to the therapeutic applications of proteins described above, biopolymers such as enzymes, peptides, and structural proteins can be used in non-therapeutic applications. These non-therapeutic biopolymers can be produced from a number of different pathways, for example, derived from plant sources, animal sources, or produced from cell cultures.

The non-therapeutic proteins can be produced, transported, stored, and handled as a granular or powdered material or as a solution or dispersion, usually in water. The biopolymers for non-therapeutic applications can be globular or fibrous proteins, and certain forms of these materials can have limited solubility in water or exhibit high viscosity upon dissolution. These solution properties can present challenges to the formulation, handling, storage, pumping, and performance of the non-therapeutic materials, so there is a need for methods to reduce viscosity and improve solubility and stability of non-therapeutic protein solutions.

Proteins are complex biopolymers, each with a uniquely folded 3-D structure and surface energy map (hydrophobic/hydrophilic regions and charges). In concentrated protein solutions, these macromolecules may strongly interact and even inter-lock in complicated ways, depending on their exact shape and surface energy distribution. "Hot-spots" for strong specific interactions lead to protein clustering, increasing solution viscosity. To address these concerns, a number of excipient compounds are used in biotherapeutic formulations, aiming to reduce solution viscosity by impeding localized interactions and clustering. These efforts are individually tailored, often empirically, sometimes guided by in silico simulations. Combinations of excipient compounds may be provided, but optimizing such combinations again must progress empirically and on a case-by case basis.

There remains a need in the art for a truly universal approach to reducing viscosity in protein formulations at a given concentration under nonlinear conditions. There is an additional need in the art to achieve this viscosity reduction while preserving the activity of the protein. It would be further desirable to adapt the viscosity-reduction system to use with formulations having tunable and sustained release profiles, and to use with formulations adapted for depot injection. In addition, it is desirable to improve processes for producing proteins and other biopolymers.

SUMMARY OF THE INVENTION

Disclosed herein, in embodiments, are liquid formulations comprising a protein and an excipient compound selected from the group consisting of hindered amines, anionic aromatics, functionalized amino acids, oligopeptides, short-chain organic acids, and low molecular weight aliphatic polyacids, wherein the excipient compound is added in a viscosity-reducing amount. In embodiments, the protein is a PEGylated protein and the excipient is a low molecular weight aliphatic polyacid. In embodiments, the formulation is a pharmaceutical composition, and the therapeutic formulation comprises a therapeutic protein, wherein the excipient compound is a pharmaceutically acceptable excipient compound. In embodiments, the formulation is a non-therapeutic formulation, and the non-therapeutic formulation comprises a non-therapeutic protein. In embodiments, the viscosity-reducing amount reduces viscosity of the formulation to a viscosity less than the viscosity of a control formulation. In embodiments, the viscosity of the formulation is at least about 10% less than the viscosity of the control formulation or is at least about 30% less than the viscosity of the control formulation, or is at least about 50% less than the viscosity of the control formulation, or is at least about 70% less than the viscosity of the control formulation, or is at least about 90% less than the viscosity of the control formulation. In embodiments, the viscosity is less than about 100 cP, or is less than about 50 cP, or is less than about 20 cP, or is less than about 10 cP. In embodiments, the excipient compound has a molecular weight of <5000 Da, or <1500 Da, or <500 Da. In embodiments, the formulation contains at least about 25 mg/mL of the protein, or at least about 100 mg/mL of the protein, or at least about 200 mg/mL of the protein, or at least about 300 mg/mL of the protein. In embodiments, the formulation comprises between about 5 mg/mL to about 300 mg/mL of the excipient compound or comprises between about 10 mg/mL to about 200 mg/mL of the excipient compound or comprises between about 20 mg/mL to about 100 mg/mL, or comprises between about 25 mg/mL to about 75 mg/mL of the excipient compound. In embodiments, the formulation has an improved stability when compared to the control formulation. In embodiments, the excipient compound is a hindered amine. In embodiments, the hindered amine is selected from the group consisting of caffeine, theophylline, tyramine, procaine, lidocaine, imidazole, aspartame, saccharin, and acesulfame potassium. In embodiments, the hindered amine is caffeine. In embodiments, the hindered amine is a local injectable anesthetic compound. The hindered amine can possess an independent pharmacological property, and the hindered amine can be present in the formulation in an amount that has an independent pharmacological effect. In embodiments the hindered amine can be present in the formulation in an amount that is less than a therapeutically effective amount. The independent pharmacological activity can be a local anesthetic activity. In embodiments, the hindered amine possessing the independent pharmacological activity is combined with a second excipient compound that further decreases the viscosity of the formulation. The second excipient compound can be selected from the group consisting of caffeine, theophylline, tyramine, procaine, lidocaine, imidazole, aspartame, saccharin, and acesulfame potassium. In embodiments, the formulation can comprise an additional agent selected from the group consisting of preservatives, surfactants, sugars, polysaccharides, arginine, proline, hyaluronidase, stabilizers, and buffers.

Further disclosed herein are methods of treating a disease or disorder in a mammal, comprising administering to said mammal a liquid therapeutic formulation, wherein the therapeutic formulation comprises a therapeutically effective amount of a therapeutic protein, and wherein the formulation further comprises an pharmaceutically acceptable excipient compound selected from the group consisting of hindered amines, anionic aromatics, functionalized amino acids, oligopeptides, short-chain organic acids, and low molecular weight aliphatic polyacids; and wherein the therapeutic formulation is effective for the treatment of the disease or disorder. In embodiments, the therapeutic protein is a PEGylated protein, and the excipient compound is a low molecular weight aliphatic polyacid. In embodiments, the excipient is a hindered amine. In embodiments, the hindered amine is a local anesthetic compound. In embodiments, the formulation is administered by subcutaneous injection, or an intramuscular injection, or an intravenous injection. In embodiments, the excipient compound is present in the therapeutic formulation in a viscosity-reducing amount, and the viscosity-reducing amount reduces viscosity of the therapeutic formulation to a viscosity less than the viscosity of a control formulation. In embodiments, the therapeutic formulation has an improved stability when compared to the control formulation. In embodiments, the excipient compound is essentially pure.

Further disclosed herein are methods of reducing pain at an injection site of a therapeutic protein in a mammal in need thereof, comprising: administering a liquid therapeutic formulation by injection, wherein the therapeutic formulation comprises a therapeutically effective amount of the therapeutic protein, wherein the formulation further comprises an pharmaceutically acceptable excipient compound selected from the group consisting of local injectable anesthetic compounds, wherein the pharmaceutically acceptable excipient compound is added to the formulation in a viscosity-reducing amount; and wherein the mammal experiences less pain with administration of the therapeutic formulation comprising the excipient compound than that with administration of a control therapeutic formulation, wherein the control therapeutic formulation does not contain the excipient compound and is otherwise identical to the therapeutic formulation.

Disclosed herein, in embodiments, are methods of improving stability of a liquid protein formulation, comprising: preparing a liquid protein formulation comprising a therapeutic protein and an excipient compound selected from the group selected from the group consisting of hindered amines, anionic aromatics, functionalized amino acids, oligopeptides, and short-chain organic acids, and low molecular weight aliphatic polyacids, wherein the liquid protein formulation demonstrates improved stability compared to a control liquid protein formulation, wherein the control liquid protein formulation does not contain the excipient compound and is otherwise identical to the liquid protein formulation. The stability of the liquid formulation can be a cold storage conditions stability, a room temperature stability or an elevated temperature stability.

Also disclosed herein, in embodiments, are liquid formulations comprising a protein and an excipient compound selected from the group consisting of hindered amines, anionic aromatics, functionalized amino acids, oligopeptides, short-chain organic acids, and low molecular weight aliphatic polyacids, wherein the presence of the excipient compound in the formulation results in improved protein-protein interaction characteristics as measured by the protein diffusion interaction parameter kD, or the second virial coefficient B22. In embodiments, the formulation is a therapeutic formulation, and comprises a therapeutic protein. In embodiments, the formulation is a non-therapeutic formulation, and comprises a non-therapeutic protein.

Further disclosed herein, in embodiments, are methods of improving a protein-related process comprising providing the liquid formulation described above, and employing it in a processing method. In embodiments, the processing method includes filtration, pumping, mixing, centrifugation, membrane separation, lyophilization, or chromatography. In embodiments, the processing method is selected from the group consisting of cell culture harvest, chromatography, viral inactivation, and filtration. In embodiments, the processing method is a chromatography process or a filtration process. In embodiments, the filtration process is a virus filtration process or an ultrafiltration/diafiltration process.

Also disclosed herein are methods of improving a parameter of a protein-related process, comprising providing a viscosity-reducing excipient additive comprising at least one excipient compound selected from the group consisting of hindered amines, anionic aromatics, functionalized amino acids, oligopeptides, short-chain organic acids, low molecular weight aliphatic polyacids, and diones and sulfones, and adding a viscosity-reducing amount of the at least one excipient compound to a carrier solution for the protein-related process, wherein the carrier solution contains a protein of interest, thereby improving the parameter. In embodiments, the parameter can be selected from the group consisting of cost of protein production, amount of protein production, rate of protein production, and efficiency of protein production. The parameter can be a proxy parameter. In embodiments, the protein-related process is an upstream processing process. The carrier solution for the upstream processing process can be a cell culture medium. In embodiments, if the carrier solution is a cell culture medium, the step of adding the excipient additive to the carrier solution comprises a first substep of adding the excipient additive to a supplemental medium to form an excipient-containing supplemental medium, and a second substep of adding the excipient-containing supplemental medium to the cell culture medium. In other embodiments, the protein-related process is a downstream processing process. The downstream process can be a chromatography process, and the chromatography process can be a Protein-A chromatography process. In embodiments, the chromatography process recovers the protein of interest, wherein the protein of interest is characterized by an improved protein-related parameter selected from the group consisting of improved purity, improved yield, fewer particles, less misfolding, or less aggregation, as compared to a control solution. In embodiments, the improved protein-related parameter is improved yield of the protein of interest from the chromatography process. In other embodiments, the protein-related process is a process selected from the group consisting of filtration, injection, syringing, pumping, mixing, centrifugation, membrane separation, and lyophilization, and the selected process can require less force than a control process. In embodiments, the protein-related process is selected from the group consisting of a cell culture process, a cell culture harvesting process, a chromatography process, a viral inactivation process, and a filtration process. In embodiments, the protein-related process is the viral inactivation process, and the viral inactivation process is conducted at a pH level of about 2.5 to about 5.0, or the viral inactivation process is conducted at a higher pH than the control process. In other embodiments, the protein-related process is the filtration process. The filtration process can be a virus removal filtration process or an ultrafiltration/diafiltration process. The filtration process can be characterized by an improved filtration-related parameter. The improved filtration-related parameter can be a faster filtration rate than the filtration rate of the control solution. The improved filtration-related parameter can be a production of a smaller amount of aggregated protein than the amount of aggregated protein produced by a control filtration process. The improved filtration-related parameter can be a higher mass transfer efficiency than the mass transfer efficiency of the control filtration process. The improved filtration-related parameter can be a higher concentration or a higher yield of the target protein than a concentration or yield of the target protein produced by the control filtration process.

Further disclosed herein are methods as described above, wherein the viscosity-reducing excipient additive comprises two or more excipient compounds. In embodiments, the at least one excipient compound is a hindered amine. In embodiments, the at least one excipient compound is selected from the group consisting of caffeine, saccharin, acesulfame potassium, aspartame, theophylline, taurine, 1-methyl-2-pyrrolidone, 2-pyrrolidinone, niacinamide, and imidazole. In embodiments, the at least one excipient compound is selected from the group consisting of caffeine, taurine, niacinamide, and imidazole. In embodiments, the at least one excipient compound is an anionic aromatic excipient, and, in some embodiments, the anionic aromatic excipient can be 4-hydroxybenzenesulfonic acid. In embodiments, the viscosity-reducing amount is between about 1 mg/mL to about 100 mg/mL of the at least one excipient compound, or the viscosity-reducing amount is between about 1 mM to about 400 mM of the at least one excipient compound, or the viscosity-reducing amount is an amount from about 2 mM to about 150 mM. In embodiments, the carrier solution comprises an additional agent selected from the group consisting of preservatives, sugars, polysaccharides, arginine, proline, surfactants, stabilizers, and buffers. In embodiments, the protein of interest is a therapeutic protein, and the therapeutic protein can be a recombinant protein, or can be selected from the group consisting of a monoclonal antibody, a polyclonal antibody, an antibody fragment, a fusion protein, a PEGylated protein, an antibody-drug conjugate, a synthetic polypeptide, a protein fragment, a lipoprotein, an enzyme, and a structural peptide. In embodiments, the methods further comprise a step of adding a second viscosity-reducing excipient to the carrier solution, wherein the step of adding the second viscosity-reducing compound adds an additional improvement to the parameter.

In addition, carrier solutions are disclosed herein, comprising a liquid medium in which is dissolved a protein of interest, and a viscosity-reducing additive, wherein the carrier solution has a lower viscosity that that of a control solution. The carrier solution can further comprise an additional agent selected from the group consisting of preservatives, sugars, polysaccharides, arginine, proline, surfactants, stabilizers, and buffers.

DETAILED DESCRIPTION

Figure 1:
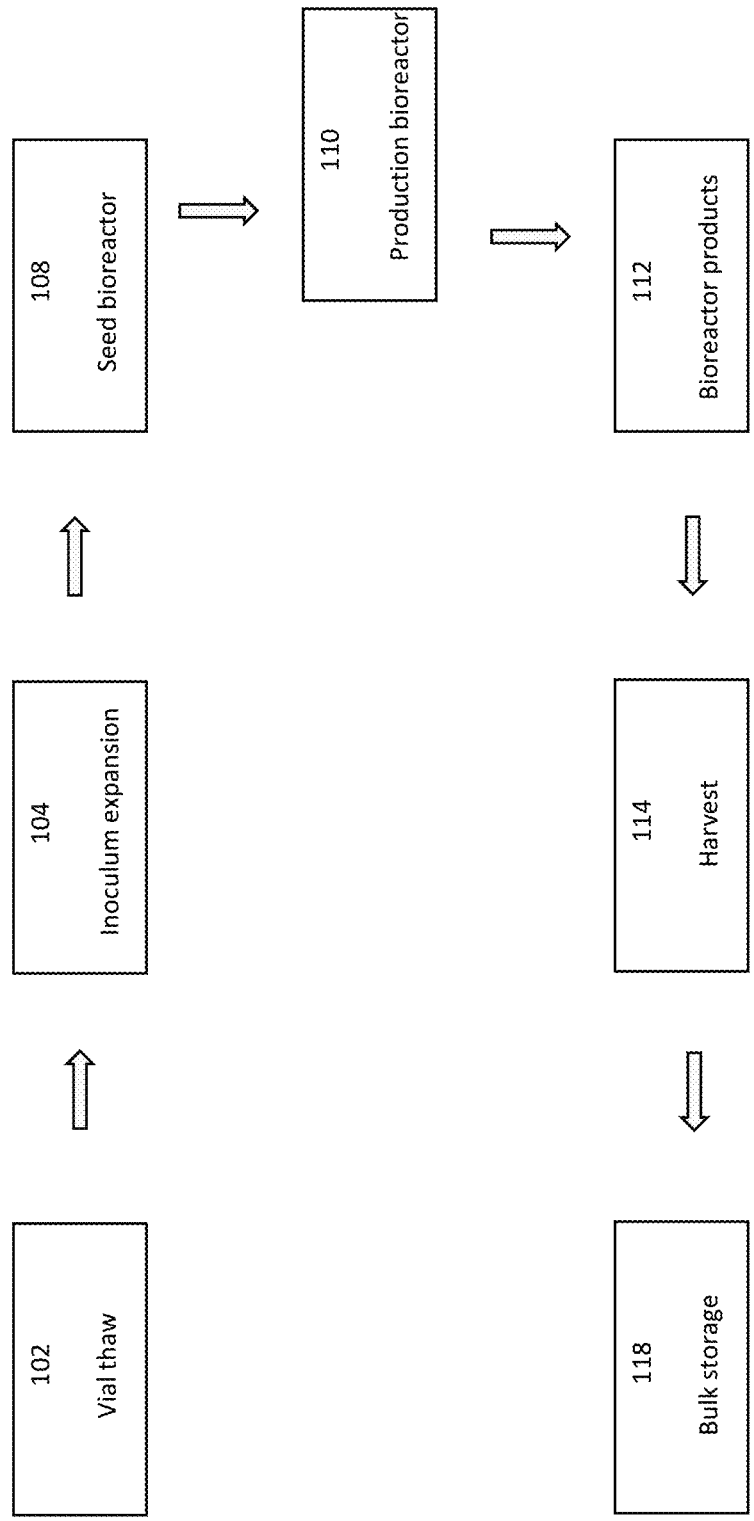
FIG. 1 presents a block diagram showing the steps in a fermentation process (an "upstream processing") for producing therapeutic proteins, for example monoclonal antibodies.

Disclosed herein are formulations and methods for their production that permit the delivery of concentrated protein solutions. In embodiments, the approaches disclosed herein can yield a lower viscosity liquid formulation or a higher concentration of therapeutic or nontherapeutic proteins in the liquid formulation, as compared to traditional protein solutions. In embodiments, the approaches disclosed herein can yield a liquid formulation having improved stability when compared to a traditional protein solution. A stable formulation is one in which the protein contained therein substantially retains its physical and chemical stability and its therapeutic or nontherapeutic efficacy upon storage under storage conditions, whether cold storage conditions, room temperature conditions, or elevated temperature storage conditions. Advantageously, a stable formulation can also offer protection against aggregation or precipitation of the proteins dissolved therein. For example, the cold storage conditions can entail storage in a refrigerator or freezer. In some examples, cold storage conditions can entail storage at a temperature of 10° or less. In additional examples, the cold storage conditions entail storage at a temperature from about 2° to about 10° C. In other examples, the cold storage conditions entail storage at a temperature of about 4° C. In additional examples, the cold storage conditions entail storage at freezing temperature such as about −20° C. or lower. In another example, cold storage conditions entail storage at a temperature of about −20° C. to about 0° C. The room temperature storage conditions can entail storage at ambient temperatures, for example, from about 10° C. to about 30° C. Elevated storage conditions can entail storage at a temperature greater. Elevated temperature stability, for example at temperatures from about 30° C. to about 50° C., can be used as part an accelerated aging study to predict the long-term storage at typical ambient (10-30° C.) conditions.

It is well known to those skilled in the art of polymer science and engineering that proteins in solution tend to form entanglements, which can limit the translational mobility of the entangled chains and interfere with the protein's therapeutic or nontherapeutic efficacy. In embodiments, excipient compounds as disclosed herein can suppress protein clustering due to specific interactions between the excipient compound and the target protein in solution. Excipient compounds as disclosed herein can be natural or synthetic, and desirably are substances that the FDA generally recognizes as safe ("GRAS").

1. Definitions

For the purpose of this disclosure, the term "protein" refers to a sequence of amino acids having a chain length long enough to produce a discrete tertiary structure, typically having a molecular weight between 1-3000 kD. In some embodiments, the molecular weight of the protein is between about 50-200 kD; in other embodiments, the molecular weight of the protein is between about 20-1000 kD or between about 20-2000 kD. In contrast to the term "protein," the term "peptide" refers to a sequence of amino acids that does not have a discrete tertiary structure. A wide variety of biopolymers are included within the scope of the term "protein." For example, the term "protein" can refer to therapeutic or non-therapeutic proteins, including antibodies, aptamers, fusion proteins, PEGylated proteins, synthetic polypeptides, protein fragments, lipoproteins, enzymes, structural peptides, and the like.

As non-limiting examples, therapeutic proteins can include mammalian proteins such as hormones and prohormones (e.g., insulin and proinsulin, glucagon, calcitonin, thyroid hormones (T3 or T4 or thyroid-stimulating hormone), parathyroid hormone, follicle-stimulating hormone, luteinizing hormone, growth hormone, growth hormone releasing factor, and the like); clotting and anti-clotting factors (e.g., tissue factor, von Willebrand's factor, Factor VIIIC, Factor IX, protein C, plasminogen activators (urokinase, tissue-type plasminogen activators), thrombin); cytokines, chemokines, and inflammatory mediators; interferons; colony-stimulating factors; interleukins (e.g., IL-1 through IL-10); growth factors (e.g., vascular endothelial growth factors, fibroblast growth factor, platelet-derived growth factor, transforming growth factor, neurotrophic growth factors, insulin-like growth factor, and the like); albumins; collagens and elastins; hematopoietic factors (e.g., erythropoietin, thrombopoietin, and the like); osteoinductive factors (e.g., bone morphogenetic protein); receptors (e.g., integrins, cadherins, and the like); surface membrane proteins; transport proteins; regulatory proteins; antigenic proteins (e.g., a viral component that acts as an antigen); and antibodies. The term "antibody" is used herein in its broadest sense, to include as non-limiting examples monoclonal antibodies (including, for example, full-length antibodies with an immunoglobulin Fc region), single-chain molecules, bi-specific and multi-specific antibodies, diabodies, antibody-drug conjugates, antibody compositions having polyepitopic specificity, polyclonal antibodies (such as polyclonal immunoglobulins used as therapies for immune-compromised patients), and fragments of antibodies (including, for example, Fc, Fab, Fv, and F(ab')2). Antibodies can also be termed "immunoglobulins." An antibody is understood to be directed against a specific protein or non-protein "antigen," which is a biologically important material; the administration of a therapeutically effective amount of an antibody to a patient can complex with the antigen, thereby altering its biological properties so that the patient experiences a therapeutic effect.

In embodiments, the proteins are PEGylated, meaning that they comprise poly(ethylene glycol) ("PEG") and/or poly(propylene glycol) ("PPG") units. PEGylated proteins, or PEG-protein conjugates, have found utility in therapeutic applications due to their beneficial properties such as solubility, pharmacokinetics, pharmacodynamics, immunogenicity, renal clearance, and stability. Non-limiting examples of PEGylated proteins are PEGylated interferons (PEG-IFN), PEGylated anti-VEGF, PEG protein conjugate drugs, Adagen, Pegaspargase, Pegfilgrastim, Pegloticase, Pegvisomant, PEGylated epoetin-β, and Certolizumab pegol.

PEGylated proteins can be synthesized by a variety of methods such as a reaction of protein with a PEG reagent having one or more reactive functional groups. The reactive functional groups on the PEG reagent can form a linkage with the protein at targeted protein sites such as lysine, histidine, cysteine, and the N-terminus. Typical PEGylation reagents have reactive functional groups such as aldehyde, maleimide, or succinimide groups that have specific reactivity with targeted amino acid residues on proteins. The PEGylation reagents can have a PEG chain length from about 1 to about 1000 PEG and/or PPG repeating units. Other methods of PEGylation include glyco-PEGylation, where the protein is first glycosylated and then the glycosylated residues are PEGylated in a second step. Certain PEGylation processes are assisted by enzymes like sialyltransferase and transglutaminase.

While the PEGylated proteins can offer therapeutic advantages over native, non-PEGylated proteins, these materials can have physical or chemical properties that make them difficult to purify, dissolve, filter, concentrate, and administer. The PEGylation of a protein can lead to a higher solution viscosity compared to the native protein, and this generally requires the formulation of PEGylated protein solutions at lower concentrations.

It is desirable to formulate protein therapeutics in stable, low viscosity solutions so they can be administered to patients in a minimal injection volume. For example, the subcutaneous (SC) or intramuscular (IM) injection of drugs generally requires a small injection volume, preferably less than 2 mL. The SC and IM injection routes are well suited to self-administered care, and this is a less costly and more accessible form of treatment compared with intravenous (IV) injection which is only conducted under direct medical supervision. Formulations for SC or IM injection require a low solution viscosity, generally below 30 cP, and preferably below 20 cP, to allow easy flow of the therapeutic solution through a narrow-gauge needle. This combination of small injection volume and low viscosity requirements present a challenge to the use of PEGylated protein therapeutics in SC or IM injection routes.

Those proteins having therapeutic effects may be termed "therapeutic proteins"; formulations containing therapeutic proteins in therapeutically effective amounts may be termed "therapeutic formulations." The therapeutic protein contained in a therapeutic formulation may also be termed its "protein active ingredient." Typically, a therapeutic formulation comprises a therapeutically effective amount of a protein active ingredient and an excipient, with or without other optional components. As used herein, the term "therapeutic" includes both treatments of existing disorders and preventions of disorders. Therapeutic proteins include, for example, proteins such as bevacizumab, trastuzumab, adalimumab, infliximab, etanercept, darbepoetin alfa, epoetin alfa, cetuximab, filgrastim, and rituximab. Other therapeutic proteins will be familiar to those having ordinary skill in the art.

A "treatment" includes any measure intended to cure, heal, alleviate, improve, remedy, or otherwise beneficially affect the disorder, including preventing or delaying the onset of symptoms and/or alleviating or ameliorating symptoms of the disorder. Those patients in need of a treatment include both those who already have a specific disorder, and those for whom the prevention of a disorder is desirable. A disorder is any condition that alters the homeostatic well-being of a mammal, including acute or chronic diseases, or pathological conditions that predispose the mammal to an acute or chronic disease. Non-limiting examples of disorders include cancers, metabolic disorders (e.g., diabetes), allergic disorders (e.g., asthma), dermatological disorders, cardiovascular disorders, respiratory disorders, hematological disorders, musculoskeletal disorders, inflammatory or rheumatological disorders, autoimmune disorders, gastrointestinal disorders, urological disorders, sexual and reproductive disorders, neurological disorders, and the like. The term "mammal" for the purposes of treatment can refer to any animal classified as a mammal, including humans, domestic animals, pet animals, farm animals, sporting animals, working animals, and the like. A "treatment" can therefore include both veterinary and human treatments. For convenience, the mammal undergoing such "treatment" can be referred to as a "patient." In certain embodiments, the patient can be of any age, including fetal animals in utero.

In embodiments, a treatment involves providing a therapeutically effective amount of a therapeutic formulation to a mammal in need thereof. A "therapeutically effective amount" is at least the minimum concentration of the therapeutic protein administered to the mammal in need thereof, to effect a treatment of an existing disorder or a prevention of an anticipated disorder (either such treatment or such prevention being a "therapeutic intervention"). Therapeutically effective amounts of various therapeutic proteins that may be included as active ingredients in the therapeutic formulation may be familiar in the art; or, for therapeutic proteins discovered or applied to therapeutic interventions hereinafter, the therapeutically effective amount can be determined by standard techniques carried out by those having ordinary skill in the art, using no more than routine experimentation.

Those proteins used for non-therapeutic purposes (i.e., purposes not involving treatments), such as household, nutrition, commercial, and industrial applications, may be termed "non-therapeutic proteins." Formulations containing non-therapeutic proteins may be termed "non-therapeutic formulations". The non-therapeutic proteins can be derived from plant sources, animal sources, or produced from cell cultures; they also can be enzymes or structural proteins. The non-therapeutic proteins can be used in household, nutrition, commercial, and industrial applications such as catalysts, human and animal nutrition, processing aids, cleaners, and waste treatment.

An important category of non-therapeutic biopolymers is enzymes. Enzymes have a number of non-therapeutic applications, for example, as catalysts, human and animal nutritional ingredients, processing aids, cleaners, and waste treatment agents. Enzyme catalysts are used to accelerate a variety of chemical reactions. Examples of enzyme catalysts for non-therapeutic uses include catalases, oxidoreductases, transferases, hydrolases, lyases, isomerases, and ligases. Human and animal nutritional uses of enzymes include nutraceuticals, nutritive sources of protein, chelation or controlled delivery of micronutrients, digestion aids, and supplements; these can be derived from amylase, protease, trypsin, lactase, and the like. Enzymatic processing aids are used to improve the production of food and beverage products in operations like baking, brewing, fermenting, juice processing, and winemaking. Examples of these food and beverage processing aids include amylases, cellulases, pectinases, glucanases, lipases, and lactases. Enzymes can also be used in the production of biofuels. Ethanol for biofuels, for example, can be aided by the enzymatic degradation of biomass feedstocks such as cellulosic and lignocellulosic materials. The treatment of such feedstock materials with cellulases and ligninases transforms the biomass into a substrate that can be fermented into fuels. In other commercial applications, enzymes are used as detergents, cleaners, and stain lifting aids for laundry, dish washing, surface cleaning, and equipment cleaning applications. Typical enzymes for this purpose include proteases, cellulases, amylases, and lipases. In addition, non-therapeutic enzymes are used in a variety of commercial and industrial processes such as textile softening with cellulases, leather processing, waste treatment, contaminated sediment treatment, water treatment, pulp bleaching, and pulp softening and debonding. Typical enzymes for these purposes are amylases, xylanases, cellulases, and ligninases.

Other examples of non-therapeutic biopolymers include fibrous or structural proteins such as keratins, collagen, gelatin, elastin, fibroin, actin, tubulin, or the hydrolyzed, degraded, or derivatized forms thereof. These materials are used in the preparation and formulation of food ingredients such as gelatin, ice cream, yogurt, and confections; they area also added to foods as thickeners, rheology modifiers, mouthfeel improvers, and as a source of nutritional protein. In the cosmetics and personal care industry, collagen, elastin, keratin, and hydrolyzed keratin are widely used as ingredients in skin care and hair care formulations. Still other examples of non-therapeutic biopolymers are whey proteins such as beta-lactoglobulin, alpha-lactalbumin, and serum albumin. These whey proteins are produced in mass scale as a byproduct from dairy operations and have been used for a variety of non-therapeutic applications.

2. Measurements

In embodiments, the protein-containing formulations described herein are resistant to monomer loss as measured by size exclusion chromatography (SEC) analysis. In SEC analysis as used herein, the main analyte peak is generally associated with the target protein contained in the formulation, and this main peak of the protein is referred to as the monomer peak. The monomer peak represents the amount of target protein, e.g., a protein active ingredient, in the monomeric state, as opposed to aggregated (dimeric, trimeric, oligomeric, etc.) or fragmented states. The monomer peak area can be compared with the total area of the monomer, aggregate, and fragment peaks associated with the target protein. Thus, the stability of a protein-containing formulation can be observed by the relative amount of monomer after an elapsed time; an improvement in stability of a protein-containing formulation of the invention can therefore be measured as a higher percent monomer after a certain elapsed time, as compared to the percent monomer in a control formulation that does not contain the excipient.

In embodiments, an ideal stability result is to have from 98 to 100% monomer peak as determined by SEC analysis. In embodiments, an improvement in stability of a protein-containing formulation of the invention can be measured as a higher percent monomer after exposure to a stress condition, as compared to the percent monomer in a control formulation that does not contain the excipient when such control formulation is exposed to the same stress condition. In embodiments, the stress conditions can be a low temperature storage, high temperature storage, exposure to air, exposure to gas bubbles, exposure to shear conditions, or exposure to freeze/thaw cycles.

In embodiments, the protein-containing formulations as described herein are resistant to an increase in protein particle size as measured by dynamic light scattering (DLS) analysis. In DLS analysis as used herein, the particle size of the protein in the protein-containing formulation can be observed as a median particle diameter. Ideally, the median particle diameter of the target protein should be relatively unchanged when subjected to DLS analysis, since the particle diameter represents the active component in the monomeric state, as opposed to aggregated (dimeric, trimeric, oligomeric, etc.) or fragmented states. An increase of the median particle diameter could represent an aggregated protein. Thus, the stability of a protein-containing formulation can be observed by the relative change in median particle diameter after an elapsed time.

In embodiments, the protein-containing formulations as described herein are resistant to forming a polydisperse particle size distribution as measured by dynamic light scattering (DLS) analysis. In embodiments, a protein-containing formulation can contain a monodisperse particle size distribution of colloidal protein particles. In embodiments, an ideal stability result is to have less than a 10% change in the median particle diameter compared to the initial median particle diameter of the formulation. In embodiments, an improvement in stability of a protein-containing formulation of the invention can be measured as a lower percent change of the median particle diameter after a certain elapsed time, as compared to the median particle diameter in a control formulation that does not contain the excipient. In embodiments, an improvement in stability of a protein-containing formulation of the invention can be measured as a lower percent change of the median particle diameter after exposure to a stress condition, as compared to the percent change of the median particle diameter in a control formulation that does not contain the excipient when such control formulation is exposed to the same stress condition. In embodiments, the stress conditions can be a low temperature storage, high temperature storage, exposure to air, exposure to gas bubbles, exposure to shear conditions, or exposure to freeze/thaw cycles. In embodiments, an improvement in stability of a protein-containing formulation therapeutic formulation of the invention can be measured as a less polydisperse particle size distribution as measured by DLS, as compared to the polydispersity of the particle size distribution in a control formulation that does not contain the excipient when such control formulation is exposed to the same stress condition.

In embodiments, the protein-containing formulations of the invention are resistant to precipitation as measured by turbidity, light scattering, and/or particle counting analysis. In turbidity, light scattering, or particle counting analysis, a lower value generally represents a lower number of suspended particles in a formulation. An increase of turbidity, light scattering, or particle counting can indicate that the solution of the target protein is not stable. Thus, the stability of a protein-containing formulation can be observed by the relative amount of turbidity, light scattering, or particle counting after an elapsed time. In embodiments, an ideal stability result is to have a low and relatively constant turbidity, light scattering, or particle counting value. In embodiments, an improvement in stability of a protein-containing formulation of the invention can be measured as a lower turbidity, lower light scattering, or lower particle count after a certain elapsed time, as compared to the turbidity, light scattering, or particle count values in a control formulation that does not contain the excipient. In embodiments, an improvement in stability of a protein-containing formulation as described herein can be measured as a lower turbidity, lower light scattering, or lower particle count after exposure to a stress condition, as compared to the turbidity, light scattering, or particle count in a control formulation that does not contain the excipient when such control formulation is exposed to the same stress condition. In embodiments, the stress conditions can be a low temperature storage, high temperature storage, exposure to air, exposure to gas bubbles, exposure to shear conditions, or exposure to freeze/thaw cycles.

3. Therapeutic Formulations

In one aspect, the formulations and methods disclosed herein provide stable liquid formulations of improved or reduced viscosity, comprising a therapeutic protein in a therapeutically effective amount and an excipient compound. In embodiments, the formulation can improve the stability while providing an acceptable concentration of active ingredients and an acceptable viscosity. In embodiments, the formulation provides an improvement in stability when compared to a control formulation; for the purposes of this disclosure, a control formulation is a formulation containing the protein active ingredient that is identical on a dry weight basis in every way to the therapeutic formulation except that it lacks the excipient compound. In embodiments, improved stability of the protein containing formulation is in the form of lower percentage of soluble aggregates, particulates, subvisible particles, or gel formation, compared to a control formulation.

It is understood that the viscosity of a liquid protein formulation can be affected by a variety of factors, including but not limited to: the nature of the protein itself (e.g., enzyme, antibody, receptor, fusion protein, etc.); its size, three-dimensional structure, chemical composition, and molecular weight; its concentration in the formulation; the components of the formulation besides the protein; the desired pH range; the storage conditions for the formulation; and the method of administering the formulation to the patient. Therapeutic proteins most suitable for use with the excipient compounds described herein are preferably essentially pure, i.e., free from contaminating proteins. In embodiments, an "essentially pure" therapeutic protein is a protein composition comprising at least 90% by weight of the therapeutic protein, or preferably at least 95% by weight, or more preferably, at least 99% by weight, all based on the total weight of therapeutic proteins and contaminating proteins in the composition. For the purposes of clarity, a protein added as an excipient is not intended to be included in this definition. The therapeutic formulations described herein are intended for use as pharmaceutical-grade formulations, i.e., formulations intended for use in treating a mammal, in such a form that the desired therapeutic efficacy of the protein active ingredient can be achieved, and without containing components that are toxic to the mammal to whom the formulation is to be administered.

In embodiments, the therapeutic formulation contains at least 25 mg/mL of protein active ingredient. In other embodiments, the therapeutic formulation contains at least 100 mg/mL of protein active ingredient. In other embodiments, the therapeutic formulation contains at least 200 mg/mL of protein active ingredient. In yet other embodiments, the therapeutic formulation solution contains at least 300 mg/mL of protein active ingredient. Generally, the excipient compounds disclosed herein are added to the therapeutic formulation in an amount between about 5 to about 300 mg/mL. In embodiments, the excipient compound can be added in an amount of about 10 to about 200 mg/mL. In embodiments, the excipient compound can be added in an amount of about 20 to about 100 mg/mL. In embodiments, the excipient can be added in an amount of about 25 to about 75 mg/mL.

Excipient compounds of various molecular weights are selected for specific advantageous properties when combined with the protein active ingredient in a formulation. Examples of therapeutic formulations comprising excipient compounds are provided below. In embodiments, the excipient compound has a molecular weight of <5000 Da. In embodiments, the excipient compound has a molecular weight of <1000 Da. In embodiments, the excipient compound has a molecular weight of <500 Da.

In embodiments, the excipient compounds disclosed herein is added to the therapeutic formulation in a viscosity-reducing amount. In embodiments, a viscosity-reducing amount is the amount of an excipient compound that reduces the viscosity of the formulation at least 10% when compared to a control formulation; for the purposes of this disclosure, a control formulation is a formulation containing the protein active ingredient that is identical on a dry weight basis in every way to the therapeutic formulation except that it lacks the excipient compound. In embodiments, the viscosity-reducing amount is the amount of an excipient compound that reduces the viscosity of the formulation at least 30% when compared to the control formulation. In embodiments, the viscosity-reducing amount is the amount of an excipient compound that reduces the viscosity of the formulation at least 50% when compared to the control formulation. In embodiments, the viscosity-reducing amount is the amount of an excipient compound that reduces the viscosity of the formulation at least 70% when compared to the control formulation. In embodiments, the viscosity-reducing amount is the amount of an excipient compound that reduces the viscosity of the formulation at least 90% when compared to the control formulation.

In embodiments, the viscosity-reducing amount yields a therapeutic formulation having a viscosity of less than 100 cP. In other embodiments, the therapeutic formulation has a viscosity of less than 50 cP. In other embodiments, the therapeutic formulation has a viscosity of less than 20 cP. In yet other embodiments, the therapeutic formulation has a viscosity of less than 10 cP. The term "viscosity" as used herein refers to a dynamic viscosity value when measured by the methods disclosed herein.

Therapeutic formulations in accordance with this disclosure have certain advantageous properties. In embodiments, the therapeutic formulations are resistant to shear degradation, phase separation, clouding out, oxidation, deamidation, aggregation, precipitation, and denaturing. In embodiments, the therapeutic formulations are processed, purified, stored, syringed, dosed, filtered, and centrifuged more effectively, compared with a control formulation. In embodiments, the therapeutic formulations are administered to a patient at high concentration of therapeutic protein. In embodiments, the therapeutic formulations are administered to patients with less discomfort than would be experienced with a similar formulation lacking the therapeutic excipient. In embodiments, the therapeutic formulations are administered as a depot injection. In embodiments, the therapeutic formulations extend the half-life of the therapeutic protein in the body.

These features of therapeutic formulations as disclosed herein would permit the administration of such formulations by intramuscular or subcutaneous injection in a clinical situation, i.e., a situation where patient acceptance of an intramuscular injection would include the use of small-bore needles typical for IM/SC purposes and the use of a tolerable (for example, 2-3 cc) injected volume, and where these conditions result in the administration of an effective amount of the formulation in a single injection at a single injection site. By contrast, injection of a comparable dosage amount of the therapeutic protein using conventional formulation techniques would be limited by the higher viscosity of the conventional formulation, so that a SC/IM injection of the conventional formulation would not be suitable for a clinical situation. High concentration solutions of therapeutic proteins formulated with the excipient compounds described herein can be administered to patients using syringes or pre-filled syringes.

In embodiments, the therapeutic excipient has antioxidant properties that stabilize the therapeutic protein against oxidative damage. In embodiments, the therapeutic formulation is stored at ambient temperatures, or for extended time at refrigerator conditions without appreciable loss of potency for the therapeutic protein. In embodiments, the therapeutic formulation is dried down for storage until it is needed; then it is reconstituted with an appropriate solvent, e.g., water. Advantageously, the formulations prepared as described herein can be stable over a prolonged period of time, from months to years. When exceptionally long periods of storage are desired, the formulations can be preserved in a freezer (and later reactivated) without fear of protein denaturation.

In embodiments, formulations can be prepared for long-term storage that do not require refrigeration.

Methods for preparing therapeutic formulations may be familiar to skilled artisans. The therapeutic formulations of the present invention can be prepared, for example, by adding the excipient compound to the formulation before or after the therapeutic protein is added to the solution. The therapeutic formulation can, for example, be produced by combining the therapeutic protein and the excipient at a first (lower) concentration and then processed by filtration or centrifugation to produce a second (higher) concentration of the therapeutic protein. Therapeutic formulations can be made with one or more of the excipient compounds with chaotropes, kosmotropes, hydrotropes, and salts. Therapeutic formulations can be made with one or more of the excipient compounds using techniques such as encapsulation, dispersion, liposome, vesicle formation, and the like. Methods for preparing therapeutic formulations comprising the excipient compounds disclosed herein can include combinations of the excipient compounds. In embodiments, combinations of excipients can produce benefits in lower viscosity, improved stability, or reduced injection site pain. Other additives may be introduced into the therapeutic formulations during their manufacture, including preservatives, surfactants, sugars, sucrose, trehalose, polysaccharides, arginine, proline, hyaluronidase, stabilizers, buffers, and the like. As used herein, a pharmaceutically acceptable excipient compound is one that is non-toxic and suitable for animal and/or human administration.

4. Non-Therapeutic Formulations

In one aspect, the formulations and methods disclosed herein provide stable liquid formulations of improved or reduced viscosity, comprising a non-therapeutic protein in an effective amount and an excipient compound. In embodiments, the formulation improves the stability while providing an acceptable concentration of active ingredients and an acceptable viscosity. In embodiments, the formulation provides an improvement in stability when compared to a control formulation; for the purposes of this disclosure, a control formulation is a formulation containing the protein active ingredient that is identical on a dry weight basis in every way to the non-therapeutic formulation except that it lacks the excipient compound.

It is understood that the viscosity of a liquid protein formulation can be affected by a variety of factors, including but not limited to: the nature of the protein itself (e.g., enzyme, structural protein, degree of hydrolysis, etc.); its size, three-dimensional structure, chemical composition, and molecular weight; its concentration in the formulation; the components of the formulation besides the protein; the desired pH range; and the storage conditions for the formulation.

In embodiments, the non-therapeutic formulation contains at least 25 mg/mL of protein active ingredient. In other embodiments, the non-therapeutic formulation contains at least 100 mg/mL of protein active ingredient. In other embodiments, the non-therapeutic formulation contains at least 200 mg/mL of protein active ingredient. In yet other embodiments, the non-therapeutic formulation solution contains at least 300 mg/mL of protein active ingredient. Generally, the excipient compounds disclosed herein are added to the non-therapeutic formulation in an amount between about 5 to about 300 mg/mL. In embodiments, the excipient compound is added in an amount of about 10 to about 200 mg/mL. In embodiments, the excipient compound is added in an amount of about 20 to about 100 mg/mL. In embodiments, the excipient is added in an amount of about 25 to about 75 mg/mL.

Excipient compounds of various molecular weights are selected for specific advantageous properties when combined with the protein active ingredient in a formulation. Examples of non-therapeutic formulations comprising excipient compounds are provided below. In embodiments, the excipient compound has a molecular weight of <5000 Da. In embodiments, the excipient compound has a molecular weight of <1000 Da. In embodiments, the excipient compound has a molecular weight of <500 Da.

In embodiments, the excipient compounds disclosed herein is added to the non-therapeutic formulation in a viscosity-reducing amount. In embodiments, a viscosity-reducing amount is the amount of an excipient compound that reduces the viscosity of the formulation at least 10% when compared to a control formulation; for the purposes of this disclosure, a control formulation is a formulation containing the protein active ingredient that is identical on a dry weight basis in every way to the therapeutic formulation except that it lacks the excipient compound. In embodiments, the viscosity-reducing amount is the amount of an excipient compound that reduces the viscosity of the formulation at least 30% when compared to the control formulation. In embodiments, the viscosity-reducing amount is the amount of an excipient compound that reduces the viscosity of the formulation at least 50% when compared to the control formulation. In embodiments, the viscosity-reducing amount is the amount of an excipient compound that reduces the viscosity of the formulation at least 70% when compared to the control formulation. In embodiments, the viscosity-reducing amount is the amount of an excipient compound that reduces the viscosity of the formulation at least 90% when compared to the control formulation.

In embodiments, the viscosity-reducing amount yields a non-therapeutic formulation having a viscosity of less than 100 cP. In other embodiments, the non-therapeutic formulation has a viscosity of less than 50 cP. In other embodiments, the non-therapeutic formulation has a viscosity of less than 20 cP. In yet other embodiments, the non-therapeutic formulation has a viscosity of less than 10 cP. The term "viscosity" as used herein refers to a dynamic viscosity value.

Non-therapeutic formulations in accordance with this disclosure can have certain advantageous properties. In embodiments, the non-therapeutic formulations are resistant to shear degradation, phase separation, clouding out, oxidation, deamidation, aggregation, precipitation, and denaturing. In embodiments, the therapeutic formulations can be processed, purified, stored, pumped, filtered, and centrifuged more effectively, compared with a control formulation.

In embodiments, the non-therapeutic excipient has anti-oxidant properties that stabilize the non-therapeutic protein against oxidative damage. In embodiments, the non-therapeutic formulation is stored at ambient temperatures, or for extended time at refrigerator conditions without appreciable loss of potency for the non-therapeutic protein. In embodiments, the non-therapeutic formulation is dried down for storage until it is needed; then it can be reconstituted with an appropriate solvent, e.g., water. Advantageously, the formulations prepared as described herein is stable over a prolonged period of time, from months to years. When exceptionally long periods of storage are desired, the formulations are preserved in a freezer (and later reactivated) without fear of protein denaturation. In embodiments, formulations are prepared for long-term storage that do not require refrigeration.

Methods for preparing non-therapeutic formulations comprising the excipient compounds disclosed herein may be familiar to skilled artisans. For example, the excipient compound can be added to the formulation before or after the non-therapeutic protein is added to the solution. The non-therapeutic formulation can be produced at a first (lower) concentration and then processed by filtration or centrifugation to produce a second (higher) concentration. Non-therapeutic formulations can be made with one or more of the excipient compounds with chaotropes, kosmotropes, hydrotropes, and salts. Non-therapeutic formulations can be made with one or more of the excipient compounds using techniques such as encapsulation, dispersion, liposome, vesicle formation, and the like. Other additives can be introduced into the non-therapeutic formulations during their manufacture, including preservatives, surfactants, stabilizers, and the like.

5. Excipient Compounds

Several excipient compounds are described herein, each suitable for use with one or more therapeutic or non-therapeutic proteins, and each allowing the formulation to be composed so that it contains the protein(s) at a high concentration. Some of the categories of excipient compounds described below are: (1) hindered amines; (2) anionic aromatics; (3) functionalized amino acids; (4) oligopeptides; (5) short-chain organic acids; (6) low-molecular-weight aliphatic polyacids; and (7) diones and sulfones. Without being bound by theory, the excipient compounds described herein are thought to associate with certain fragments, sequences, structures, or sections of a therapeutic protein that otherwise would be involved in inter-particle (i.e., protein-protein) interactions. The association of these excipient compounds with the therapeutic or non-therapeutic protein can mask the inter-protein interactions such that the proteins can be formulated in high concentration without causing excessive solution viscosity. Excipient compounds advantageously can be water-soluble, therefore suitable for use with aqueous vehicles. In embodiments, the excipient compounds have a water solubility of >10 mg/mL. In embodiments, the excipient compounds have a water solubility of >100 mg/mL. In embodiments, the excipient compounds have a water solubility of >500 mg/mL. Advantageously for therapeutic proteins, the excipient compounds can be derived from materials that are biologically acceptable and are non-immunogenic, and are thus suitable for pharmaceutical use. In therapeutic embodiments, the excipient compounds can be metabolized in the body to yield biologically compatible and non-immunogenic byproducts.

a. Excipient Compound Category 1: Hindered Amines

High concentration solutions of therapeutic or non-therapeutic proteins can be formulated with hindered amine small molecules as excipient compounds. As used herein, the term "hindered amine" refers to a small molecule containing at least one bulky or sterically hindered group, consistent with the examples below. Hindered amines can be used in the free base form, in the protonated form, or a combination of the two. In protonated forms, the hindered amines can be associated with an anionic counterion such as chloride, hydroxide, bromide, iodide, fluoride, acetate, formate, phosphate, sulfate, or carboxylate. Hindered amine compounds useful as excipient compounds can contain secondary amine, tertiary amine, quaternary ammonium, pyridinium, pyrrolidone, pyrrolidine, piperidine, morpholine, or guanidinium groups, such that the excipient compound has a cationic charge in aqueous solution at neutral pH. The hindered amine compounds also contain at least one bulky or sterically hindered group, such as cyclic aromatic, cycloaliphatic, cyclohexyl, or alkyl groups. In embodiments, the sterically hindered group can itself be an amine group such as a dialkylamine, trialkylamine, guanidinium, pyridinium, or quaternary ammonium group. Without being bound by theory, the hindered amine compounds are thought to associate with aromatic sections of the proteins such as phenylalanine, tryptophan, and tyrosine, by a cation pi interaction. In embodiments, the cationic group of the hindered amine can have an affinity for the electron rich pi structure of the aromatic amino acid residues in the protein, so that they can shield these sections of the protein, thereby decreasing the tendency of such shielded proteins to associate and agglomerate.

In embodiments, the hindered amine excipient compounds has a chemical structure comprising imidazole, imidazoline, or imidazolidine groups, or salts thereof, such as imidazole, 1-methylimidazole, 4-methylimidazole, 1-hexyl-3-methylimidazolium chloride, histamine, 4-methylhistamine, alpha-methylhistamine, betahistine, beta-alanine, 2-methyl-2-imidazoline, 1-butyl-3-methylimidazolium chloride, uric acid, potassium urate, betazole, carnosine, aspartame, saccharin, acesulfame potassium, xanthine, theophylline, theobromine, caffeine, and anserine. In embodiments, the hindered amine excipient compounds is selected from the group consisting of dimethylethanolamine, dimethylaminopropylamine, triethanolamine, dimethylbenzylamine, dimethylcyclohexylamine, diethylcyclohexylamine, dicyclohexylmethylamine, hexamethylene biguanide, poly(hexamethylene biguanide), imidazole, dimethylglycine, agmatine, diazabicyclo[2.2.2]octane, tetramethylethylenediamine, N,N-dimethylethanolamine, ethanolamine phosphate, glucosamine, choline chloride, phosphocholine, niacinamide, isonicotinamide, N,N-diethyl nicotinamide, nicotinic acid sodium salt, tyramine, 3-aminopyridine, 2,4,6-trimethylpyridine, 3-pyridine methanol, nicotinamide adenosine dinucleotide, biotin, morpholine, N-methylpyrrolidone, 2-pyrrolidinone, procaine, lidocaine, dicyandiamide-taurine adduct, 2-pyridylethylamine, dicyandiamide-benzyl amine adduct, dicyandiamide-alkylamine adduct, dicyandiamide-cycloalkylamine adduct, and dicyandiamide-aminomethanephosphonic acid adducts. In embodiments, a hindered amine compound consistent with this disclosure is formulated as a protonated ammonium salt. In embodiments, a hindered amine compound consistent with this disclosure is formulated as a salt with an inorganic anion or organic anion as the counterion. In embodiments, high concentration solutions of therapeutic or non-therapeutic proteins are formulated with a combination of caffeine with a benzoic acid, a hydroxybenzoic acid, or a benzenesulfonic acid as excipient compounds. In embodiments, the hindered amine excipient compounds are metabolized in the body to yield biologically compatible byproducts. In some embodiments, the hindered amine excipient compound is present in the formulation at a concentration of about 250 mg/ml or less. In additional embodiments, the hindered amine excipient compound is present in the formulation at a concentration of about 10 mg/ml to about 200 mg/ml. In yet additional aspects, the hindered amine excipient compound is present in the formulation at a concentration of about 20 to about 120 mg/ml.

In embodiments, certain hindered amine excipient compounds can possess other pharmacological properties. As examples, xanthines are a category of hindered amines having independent pharmacological properties, including stimulant properties and bronchodilator properties when systemically absorbed. Representative xanthines include caffeine, aminophylline, 3-isobutyl-1-methylxanthine, paraxanthine, pentoxifylline, theobromine, theophylline, and the like. Methylated xanthines are understood to affect force of cardiac contraction, heart rate, and bronchodilation. In some embodiments, the xanthine excipient compound is present in the formulation at a concentration of about 30 mg/ml or less.

Another category of hindered amines having independent pharmacological properties are the local injectable anesthetic compounds. Local injectable anesthetic compounds are hindered amines that have a three-component molecular structure of (a) a lipophilic aromatic ring, (b) an intermediate ester or amide linkage, and (c) a secondary or tertiary amine. This category of hindered amines is understood to interrupt neural conduction by inhibiting the influx of sodium ions, thereby inducing local anesthesia. The lipophilic aromatic ring for a local anesthetic compound may be formed of carbon atoms (e.g., a benzene ring) or it may comprise heteroatoms (e.g., a thiophene ring). Representative local injectable anesthetic compounds include, but are not limited to, amylocaine, articaine, bupivicaine, butacaine, butanilicaine, chlorprocaine, cocaine, cyclomethycaine, dimethocaine, editocaine, hexylcaine, isobucaine, levobupivacaine, lidocaine, metabutethamine, metabutoxycaine, mepivacaine, meprylcaine, propoxycaine, prilocaine, procaine, piperocaine, tetracaine, trimecaine, and the like. The local injectable anesthetic compounds can have multiple benefits in protein therapeutic formulations, such as reduced viscosity, improved stability, and reduced pain upon injection. In some embodiments, the local anesthetic compound is present in the formulation in a concentration of about 50 mg/ml or less.

In embodiments, a hindered amine having independent pharmacological properties is used as an excipient compound in accordance with the formulations and methods described herein. In some embodiments, the excipient compounds possessing independent pharmacological properties are present in an amount that does not have a pharmacological effect and/or that is not therapeutically effective. In other embodiments, the excipient compounds possessing independent pharmacological properties are present in an amount that does have a pharmacological effect and/or that is therapeutically effective. In certain embodiments, a hindered amine having independent pharmacological properties is used in combination with another excipient compound that has been selected to decrease formulation viscosity, where the hindered amine having independent pharmacological properties is used to impart the benefits of its pharmacological activity. For example, a local injectable anesthetic compound can be used to decrease formulation viscosity and also to reduce pain upon injection of the formulation. The reduction of injection pain can be caused by anesthetic properties; also, a lower injection force can be required when the viscosity is reduced by the excipients. Alternatively, a local injectable anesthetic compound can be used to impart the desirable pharmacological benefit of decreased local sensation during formulation injection, while being combined with another excipient compound that reduces the viscosity of the formulation.

b. Excipient Compound Category 2: Anionic Aromatics

High concentration solutions of therapeutic or non-therapeutic proteins can be formulated with anionic aromatic small molecule compounds as excipient compounds. The anionic aromatic excipient compounds can contain an aromatic functional group such as phenyl, benzyl, aryl, alkylbenzyl, hydroxybenzyl, phenolic, hydroxyaryl, heteroaromatic group, or a fused aromatic group. The anionic aromatic excipient compounds also can contain an anionic functional group such as carboxylate, oxide, phenoxide, sulfonate, sulfate, phosphonate, phosphate, or sulfide. While the anionic aromatic excipients might be described as an acid, a sodium salt, or other, it is understood that the excipient can be used in a variety of salt forms. Without being bound by theory, an anionic aromatic excipient compound is thought to be a bulky, sterically hindered molecule that can associate with cationic segments of a protein, so that they can shield these sections of the protein, thereby decreasing the interactions between protein molecules that render the protein-containing formulation viscous.

In embodiments, examples of anionic aromatic excipient compounds include compounds such as salicylic acid, aminosalicylic acid, hydroxybenzoic acid, aminobenzoic acid, para-aminobenzoic acid, benzenesulfonic acid, hydroxybenzenesulfonic acid, naphthalenesulfonic acid, naphthalenedisulfonic acid, hydroquinone sulfonic acid, sulfanilic acid, vanillic acid, vanillin, vanillin-taurine adduct, aminophenol, anthranilic acid, cinnamic acid, coumaric acid, adenosine monophosphate, indole acetic acid, potassium urate, furan dicarboxylic acid, furan-2-acrylic acid, 2-furanpropionic acid, sodium phenylpyruvate, sodium hydroxyphenylpyruvate, dihydroxybenzoic acid, trihydroxybenzoic acid, pyrogallol, benzoic acid, and the salts of the foregoing acids. In embodiments, the anionic aromatic excipient compounds are formulated in the ionized salt form. In embodiments, an anionic aromatic compound is formulated as the salt of a hindered amine, such as dimethylcyclohexylammonium hydroxybenzoate. In embodiments, the anionic aromatic excipient compounds are formulated with various counterions such as organic cations. In embodiments, high concentration solutions of therapeutic or non-therapeutic proteins is formulated with anionic aromatic excipient compounds and caffeine. In embodiments, the anionic aromatic excipient compounds are metabolized in the body to yield biologically compatible byproducts.

c. Excipient Compound Category 3: Functionalized Amino Acids

High concentration solutions of therapeutic or non-therapeutic proteins can be formulated with one or more functionalized amino acids, where a single functionalized amino acid or an oligopeptide comprising one or more functionalized amino acids may be used as the excipient compound. In embodiments, the functionalized amino acid compounds comprise molecules ("amino acid precursors") that can be hydrolyzed or metabolized to yield amino acids. In embodiments, the functionalized amino acids can contain an aromatic functional group such as phenyl, benzyl, aryl, alkylbenzyl, hydroxybenzyl, hydroxyaryl, heteroaromatic group, or a fused aromatic group. In embodiments, the functionalized amino acid compounds can contain esterified amino acids, such as methyl, ethyl, propyl, butyl, benzyl, cycloalkyl, glyceryl, hydroxyethyl, hydroxypropyl, PEG, and PPG esters. In embodiments, the functionalized amino acid compounds are selected from the group consisting of arginine ethyl ester, arginine methyl ester, arginine hydroxyethyl ester, and arginine hydroxypropyl ester. In embodiments, the functionalized amino acid compound is a charged ionic compound in aqueous solution at neutral pH. For example, a single amino acid can be derivatized by forming an ester, like an acetate or a benzoate, and the hydrolysis products would be acetic acid or benzoic acid, both natural materials, plus the amino acid. In embodiments, the functionalized amino acid excipient compounds are metabolized in the body to yield biologically compatible byproducts.

d. Excipient Compound Category 4: Oligopeptides

High concentration solutions of therapeutic or non-therapeutic proteins can be formulated with oligopeptides as excipient compounds. In embodiments, the oligopeptide is designed such that the structure has a charged section and a bulky section. In embodiments, the oligopeptides consist of between 2 and 10 peptide subunits. The oligopeptide can be bi-functional, for example a cationic amino acid coupled to a non-polar one, or an anionic one coupled to a non-polar one. In embodiments, the oligopeptides consist of between 2 and 5 peptide subunits. In embodiments, the oligopeptides are homopeptides such as polyglutamic acid, polyaspartic acid, poly-lysine, poly-arginine, and poly-histidine. In embodiments, the oligopeptides have a net cationic charge. In other embodiments, the oligopeptides are heteropeptides, such as Trp2Lys3. In embodiments, the oligopeptide can have an alternating structure such as an ABA repeating pattern. In embodiments, the oligopeptide can contain both anionic and cationic amino acids, for example, Arg-Glu. Without being bound by theory, the oligopeptides comprise structures that can associate with proteins in such a way that it reduces the intermolecular interactions that lead to high viscosity solutions; for example, the oligopeptide-protein association can be a charge-charge interaction, leaving a somewhat non-polar amino acid to disrupt hydrogen bonding of the hydration layer around the protein, thus lowering viscosity. In some embodiments, the oligopeptide excipient is present in the composition in a concentration of about 50 mg/ml or less.

e. Excipient Compound Category 5: Short-Chain Organic Acids

As used herein, the term "short-chain organic acids" refers to C2-C6 organic acid compounds and the salts, esters, or lactones thereof. This category includes saturated and unsaturated carboxylic acids, hydroxy functionalized carboxylic acids, and linear, branched, or cyclic carboxylic acids. In embodiments, the acid group in the short-chain organic acid is a carboxylic acid, sulfonic acid, phosphonic acid, or a salt thereof.

In addition to the four excipient categories above, high concentration solutions of therapeutic or non-therapeutic proteins can be formulated with short-chain organic acids, for example, the acid or salt forms of sorbic acid, valeric acid, propionic acid, caproic acid, and ascorbic acid as excipient compounds. Examples of excipient compounds in this category include potassium sorbate, taurine, calcium propionate, magnesium propionate, and sodium ascorbate.

f. Excipient Compound Category 6: Low Molecular Weight Aliphatic Polyacids

High concentration solutions of therapeutic or non-therapeutic PEGylated proteins can be formulated with certain excipient compounds that enable lower solution viscosity, where such excipient compounds are low molecular weight aliphatic polyacids. As used herein, the term "low molecular weight aliphatic polyacids" refers to organic aliphatic polyacids having a molecular weight <about 1500, and having at least two acidic groups, where an acidic group is understood to be a proton-donating moiety. Non-limiting examples of acidic groups include carboxylate, phosphonate, phosphate, sulfonate, sulfate, nitrate, and nitrite groups. Acidic groups on the low molecular weight aliphatic polyacid can be in the anionic salt form such as carboxylate, phosphonate, phosphate, sulfonate, sulfate, nitrate, and nitrite; their counterions can be sodium, potassium, lithium, and ammonium. Specific examples of low molecular weight aliphatic polyacids useful for interacting with PEGylated proteins as described herein include maleic acid, tartaric acid, glutaric acid, malonic acid, citric acid, ethylenediaminetetraacetic acid (EDTA), aspartic acid, glutamic acid, alendronic acid, etidronic acid and salts thereof. Further examples of low molecular weight aliphatic polyacids in their anionic salt form include phosphate ($PO_4^{3-}$), hydrogen phosphate ($HPO_4^{3-}$), dihydrogen phosphate ($H_2PO_4^{-}$), sulfate ($SO_4^{2-}$), bisulfate ($HSO_4^{-}$), pyrophosphate ($P_2O_7^{4-}$), carbonate ($CO_3^{2-}$), and bicarbonate ($HCO_3^{-}$). The counterion for the anionic salts can be Na, Li, K, or ammonium ion. These excipients can also be used in combination with excipients. As used herein, the low molecular weight aliphatic polyacid can also be an alpha hydroxy acid, where there is a hydroxyl group adjacent to a first acidic group, for example glycolic acid, lactic acid, and gluconic acid and salts thereof. In embodiments, the low molecular weight aliphatic polyacid is an oligomeric form that bears more than two acidic groups, for example polyacrylic acid, polyphosphates, polypeptides and salts thereof. In some embodiments, the low molecular weight aliphatic polyacid excipient is present in the composition in a concentration of about 50 mg/ml or less.

g. Excipient Compound Category 7: Diones and Sulfones

An effective viscosity-reducing excipient can be a molecule containing a sulfone, sulfonamide, or dione functional group that is soluble in pure water to at least 1 g/L at 298K and having a net neutral charge at pH 7. Preferably, the molecule has a molecular weight of less than 1000 g/mol and more preferably less than 500 g/mol. The diones and sulfones effective in reducing viscosity have multiple double bonds, are water soluble, have no net charge at pH 7, and are not strong hydrogen bonding donors. Not to be bound by theory, the double bond character can allow for weak pi-stacking interactions with protein. In embodiments, at high protein concentrations and in proteins that only develop high viscosity at high concentration, charged excipients are not effective because electrostatic interaction is a longer-range interaction. Solvated protein surfaces are predominantly hydrophilic, making them water soluble. The hydrophobic regions of proteins are generally shielded within the 3-dimensional structure, but the structure is constantly evolving, unfolding, and re-folding (sometimes called "breathing") and the hydrophobic regions of adjacent proteins can come into contact with each other, leading to aggregation by hydrophobic interactions. The pi-stacking feature of dione and sulfone excipients can mask hydrophobic patches that may be exposed during such "breathing." Another other important role of the excipient can be to disrupt hydrophobic interactions and hydrogen bonding between proteins in close proximity, which will effectively reduce solution viscosity. Dione and sulfone compounds that fit this description include dimethylsulfone, ethyl methyl sulfone, ethyl methyl sulfonyl acetate, ethyl isopropyl sulfone, bis(methylsulfonyl)methane, methane sulfonamide, methionine sulfone, 1,2-cyclopentanedione, 1,3-cyclopentanedione, 1,4-cyclopentanedione, and butane-2,3-dione.

6. Protein/Excipient Solutions: Properties and Processes

In certain embodiments, solutions of therapeutic or non-therapeutic proteins formulated with above-identified excipient compounds or combinations thereof (hereinafter, "excipient additives"), such as hindered amines, anionic aromatics, functionalized amino acids, oligopeptides, or short-chain organic acids, low molecular weight aliphatic polyacids, and diones and sulfones result in improved protein-protein interaction characteristics as measured by the protein diffusion interaction parameter, kD, or the second virial coefficient, B22. As used herein, an "improvement" in one or more protein-protein interaction parameters achieved by test formulations using the above-identified excipient compounds or combinations thereof can refer to a decrease in attractive protein-protein interactions when a test formulation is compared under comparable conditions with a comparable formulation that does not contain the excipient compounds or excipient additives. Such improvements can be identified by measuring certain parameters that apply to the overall process or an aspect thereof, where a parameter is any metric pertaining to the process where an alteration can be can be quantified and compared to a previous state or to a control. A parameter can pertain to the process itself, such as its efficiency, cost, yield, or rate.

A parameter can also be a proxy parameter that pertains to a feature or an aspect of the larger process. As an example, parameters such as the kD or B22 parameters can be termed proxy parameters. Measurements of kD and B22 can be made using standard techniques in the industry, and can be an indicator of process-related parameters such as improved solution properties or stability of the protein in solution. Not to be bound by theory, it is understood that a highly negative kD value can indicate that the protein has strong attractive interactions, and this can lead to aggregation, instability, and rheology problems. When formulated in the presence of certain of the above-identified excipient compounds or combinations thereof, the same protein can have an improved proxy parameter of a less negative kD value, or a kD value near or above zero, with this improved proxy parameter being associated with an improvement in a process-related parameter.

In embodiments, certain of the above-described excipient compounds or combinations thereof, such as hindered amines, anionic aromatics, functionalized amino acids, oligopeptides, short-chain organic acids, low molecular weight aliphatic polyacids, and/or diones and sulfones are used to improve a protein-related process, such as the manufacture, processing, sterile filling, purification, and analysis of protein-containing solutions, using processing methods such as filtration, syringing, transferring, pumping, mixing, heating or cooling by heat transfer, gas transfer, centrifugation, chromatography, membrane separation, centrifugal concentration, tangential flow filtration, radial flow filtration, axial flow filtration, lyophilization, and gel electrophoresis. In these and related protein-related processes, the protein of interest is dissolved in a solution that conveys it through the processing apparatus. Such solutions, referred to herein as "carrier solutions," can include cell culture media (containing, for example, secreted proteins of interest), lysate solutions following the lysis of host cells (where the protein of interest resides in the lysate), elution solutions (which contain the protein of interest following chromatographic separations), electrophoresis solutions, transport solutions for carrying the protein of interest through conduits in a processing apparatus, and the like. A carrier solution containing the protein of interest may also be termed a protein-containing solution or a protein solution. As described in more detail below, one or more viscosity-reducing excipients can be added to the protein-containing solution to improve various aspects of processing. As used herein, the terms "improve," "improvements," and the like refer to an advantageous change in a parameter of interest in a carrier solution when that parameter is compared to the same parameter as measured in a control solution. As used herein, a "control solution" means a solution that lacks the viscosity-reducing excipient but otherwise substantially similar to the carrier solution. As used herein, a "control process," for example a control filtration process, a control chromatographic process, and the like, is a protein-related process that is substantially similar to the protein-related process of interest and is performed with a control solution instead of a carrier solution.

For example, in processes where a protein-containing solution is pumped through conduits (e.g., flow chambers, piping or tubing), adding a viscosity-lowering excipient to the protein solution, as described above, before or during the pumping process can substantially reduce the force and the power required to pump the solution. It is understood that fluids generally exhibit a resistance to flow, i.e., a viscosity, and that a force must be applied to the fluid to overcome this viscosity in order to induce and propagate flow. The power, P, required for pumping scales with the head, H, and capacity, Q, as shown in the following equation:

$$P \sim HQ \tag{Eq. 1}$$

Viscous fluids tend to increase the power requirements for pumps, to lower pump efficiency, to decrease pump head and capacity, and to increase frictional resistance in piping. Adding the viscosity-lowering excipients described above to a protein solution prior to or during pumping can substantially lower processing costs by decreasing either the head (H, Eq. 1) or the capacity (Q, Eq. 1) or both. The benefits of reduced viscosity can be manifested, for example, by improved throughput, increased yield, or decreased processing time. Moreover, frictional losses from the transmission of a fluid through a conduit can account for a significant fraction of the costs associated with conveying such fluids. Adding a viscosity-lowering excipient as described above to a protein solution prior to or during pumping can substantially lower processing costs by decreasing the friction accompanying the pumping process. Measurement of processing costs represents a processing parameter that can be improved by using a viscosity-reducing excipient.

These processes and processing methods for protein solutions can have improved efficiency due to the lower viscosity, improved solubility, or improved stability of the proteins in the solution during manufacture, processing, purification, and analysis steps. Measurement of processing efficiency or measurement of proxy parameters such as viscosity, solubility or stability of the proteins in solution represent processing parameters that can be improved by using a viscosity-reducing excipient. Several different factors are understood to adversely affect protein viscosity, solubility, and stability during processing. For example, protein-containing solutions are subject to a variety of physical stressors during manufacturing and purification, including significant shear stresses induced by manipulating protein solutions through typical processing operations, including, but not limited to, pumping, mixing, centrifugation, and filtration. In addition, during these processing steps, air bubbles can become entrained within the fluid to which proteins can adsorb. Such interfacial tension forces, coupled with typical shear stresses encountered during processing, can cause adsorbed protein molecules to unfold and aggregate. Additionally, significant protein unfolding can occur during pump cavitation events and during exposure to solid surfaces during manufacturing, such as ultrafiltration and diafiltration membranes. Such events can impair protein folding and product quality.

For Newtonian fluids, the stress, $\tau$, imposed by a given process scales with the shear rate, $\dot{\gamma}$, and viscosity of the fluid, $\eta$, as shown in the following equation:

$$\tau = \dot{\gamma}\eta \qquad \text{(Eq. 2)}$$

By formulating a protein solution with one or more of the above-described excipient compounds or combinations thereof, solution viscosity is decreased, thus decreasing the shear stress encountered by the protein solution. The decreased shear stress can improve the stability of the formulation being processed, as manifested, for example, by a better or more desirable measurement of a processing parameter. Such improved processing parameters can include metrics such as reduced levels of protein aggregates, particles, or subvisible particles (manifested macroscopically as turbidity), reduced product losses, or improved overall yield. As another example of an improved processing parameter, reducing viscosity of a protein-containing solution can decrease the processing time for the solution. The processing time for a given unit operation generally scales inversely with the shear rate. Therefore, for a given characteristic stress, a decrease in protein solution viscosity by the addition of the above-described excipient compounds or combinations thereof is associated with an increase in shear rate ($\dot{\gamma}$, see Eq. 2), and therefore a decrease in the processing time.

During processing, it is understood that a protein in a solution may be a desired protein active ingredient, for example a therapeutic or non-therapeutic protein. Facilitating the processing of such a protein active ingredient using the excipients described herein can increase the yield or the rate of production of the protein active ingredient, or improve the efficiency of the particular process, or decrease the energy use, or the like, any of which outcomes represent processing parameters that have been improved by the use of the viscosity-reducing excipient. It is also understood that protein contaminants can be formed during certain processing technologies, for example during the fermentation and purification steps of bioprocessing. Removing the contaminants more quickly, more thoroughly, or more efficiently can also improve the processing of the desired protein, i.e., the protein active ingredient; these outcomes represent processing parameters that have been improved by the use of the viscosity-reducing excipient compound or additive. As described herein, certain excipients as described herein, by lowering solution viscosity, improving protein stability, and/or increasing protein solubility, can improve the transport of desired protein active ingredients, and can improve the removal of undesirable protein contaminants; both effects, which represent processing parameters that have been improved by the use of the viscosity-reducing excipient or additive, show that these excipients or additives improve the overall process of protein manufacture.

Specific platform unit operation for therapeutic protein production and purification offer further examples of the advantageous uses of viscosity-reducing excipients as disclosed herein, and further examples of these excipients' or additives' improving processing parameters. For example, introducing one or more of the viscosity-reducing excipients described above into these production and purification processes, as described below, can provide substantial improvements in molecule stability and recovery, and a decrease in operation costs.

It is understood in the art that the widely-practiced technology for producing and purifying therapeutic proteins like monoclonal antibodies generally consists of a fermentation process followed by a series of steps for purification processing. Fermentation, or upstream processing (USP), comprises those steps by which therapeutic proteins are grown in bioreactors, typically using bacterial or mammalian cell lines. USP may, in embodiments, include steps such as those shown in FIG. 1. Purification, or downstream processing (DSP) may, in embodiments, include steps such as those shown in FIG. 2.

Figure 2:
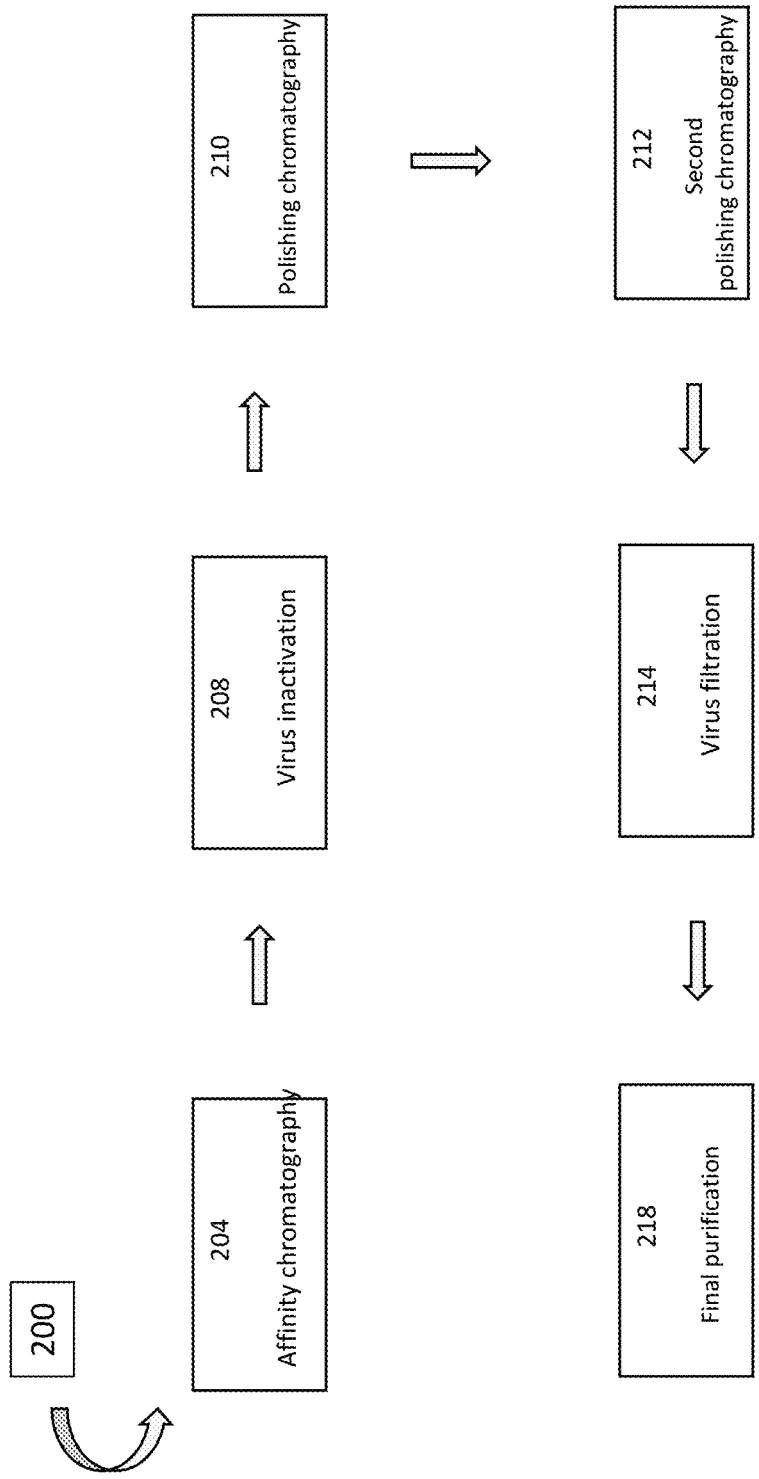
FIG. 2 presents a block diagram showing the steps in a purification process (a "downstream processing") for producing therapeutic proteins, for example monoclonal antibodies.

As shown in FIG. 1, USP may commence with the step 102 of thawing of vials from a master cell bank (MCB). The MCB can be expanded as shown in step 104, to form a working cell bank (not shown) and/or to produce the working stock for further production. Cell culture takes place in a series of seed and production bioreactors, as shown in steps 108 and 110, to yield those bioreactor products 112 from which the desired therapeutic protein can be harvested, as shown in step 114. Following harvest 114, the products can be submitted to further purification (i.e., DSP, as described below in more detail and as depicted in FIG. 2), or these products may be stored in bulk, typically by freezing and storing at a temperature of approximately −80° C.°.

In embodiments, protein production by cell culture techniques can be improved by the use of the above-identified excipients, as manifested by improvements in process-related parameters. In embodiments, the desired excipient can be added during USP in an amount effective to reduce the viscosity of the cell culture medium by at least 20%. In other embodiments, the desired excipient can be added during USP in an amount effective to reduce the viscosity of the cell culture medium by at least 30%. In embodiments, the desired excipient can be added to the cell culture medium in an amount of about 1 mM to about 400 mM. In embodiments, the desired excipient can be added to the cell culture medium in an amount of about 20 mM to about 200 mM. In embodiments, the desired excipient can be added to the cell culture medium in an amount of about 25 mM to about 100 mM. The desired excipient or combination of excipients can be added directly to the cell culture medium, or it can be added as a component of a more complex supplemental medium, for example a nutrient-containing solution or "feed solution" that is formulated separately and added to the cell culture medium. In embodiments, a second viscosity-reducing compound can be added to the carrier solution, either directly or via a supplemental medium, wherein the second viscosity-reducing compound adds an additional improvement to a particular parameter of interest.

As described below, there are many process-related parameters during USP that can be improved by use of one or more viscosity-reducing excipients. For example, in embodiments, use of a viscosity-reducing excipient can improve parameters such as the rate and/or degree of cell growth during steps such as inoculum expansion 104, and cell culture 108 and 110, and/or can improve proxy parameters that are correlated with the improvement in various process parameters. For example, adding the above-identified excipients to the USP process at a step such as the production bioreactor step 110, can decrease the viscosity of the cell culture medium, which can subsequently improve heat transfer efficiency and gas transfer efficiency. Because the cell culture process requires oxygen infusion to the cells to enable protein expression, and the diffusion of oxygen into the cells can therefore be a rate-limiting step, improving the rate of oxygen uptake by improving gas transfer efficiency through decreasing solution viscosity can improve the rate or amount of protein expression and/or its efficiency. In this context, parameters such as the rate of oxygen uptake and the rate of gas transfer efficiency can be deemed proxy parameters, whose improvement is correlated with an improvement in the process parameter of improved protein expression or improved processing efficiency. As another example, the availability of viscosity-reducing excipients can improve processing, for example, during the inoculum expansion step 104 and during the cell culture steps 108 and 110, by improving a proxy parameter such as the solubility of protein growth factors that are required for protein expression; with improved growth factor solubility, these substances can become more available to the cells, thereby facilitating cell growth.

In embodiments, process parameters such as the amount of protein recovery or the rate of protein recovery during USP can be improved by reducing viscosity during USP by several mechanisms. For example, the harvest of therapeutic protein at the end of the lysis step during harvest 114 from the completed cell culture can be more efficient or can be otherwise improved with the use of the above-identified excipients. Not to be bound by theory, by reducing viscosity of the expressed protein, these viscosity-reducing excipients can increase the efficiency of diffusion of therapeutic protein away from other lysate components. In addition, the separation of membranes and other cell debris from the protein-containing supernate can be accomplished with a faster separation rate or a higher degree of supernate purity, with the use of the viscosity-reducing excipients, thereby improving the process parameter of USP efficiency. Furthermore, the protein separation steps that use centrifugation or filtration steps can be accomplished faster with the use of the viscosity-reducing excipients, since the excipients reduce the viscosity of the medium.

In embodiments, as an additional benefit, use of the above-described viscosity-reducing excipients in cell culture can increase a process parameter such as protein yield during USP because protein misfolding and aggregation are reduced. It is understood that, as the cell culture is optimized to produce a maximum yield of recombinant protein, the resulting protein is expressed in a highly concentrated manner, which can result in misfolding; adding a viscosity-reducing excipient can reduce the attractive protein-protein interactions that lead to misfolding and aggregation, thereby increasing the amount of intact recombinant protein that is available for harvest 114.

Downstream processing (DSP), depicted in FIG. 2 in an illustrative embodiment, involves a sequence of steps that results in the recovery and purification of therapeutic proteins, for example monoclonal antibodies, biopharmaceuticals, vaccines, and other biologics. At the end of USP, the therapeutic protein of interest can be dissolved in the cell culture medium, having been secreted from the host cells. The therapeutic protein can also be dissolved in a fluid medium following the lysis of the host cells at the end of the USP sequences. DSP is undertaken to retrieve the protein of interest from the solution in which it is dissolved (e.g., the culture medium or host cell lysate medium), and to purify it. During DSP, (i) various contaminants (such as insoluble cell debris and particulates) are removed from the media, (ii) the protein product is isolated through techniques such as extraction, precipitation, adsorption or ultrafiltration, (iii) the protein product is purified through techniques such as affinity chromatography, precipitation, or crystallization, and (iv) the product is further polished, and viruses are removed.

As shown in FIG. 2, a feedstock from cell culture harvest 200 (also as described in FIG. 1) is initially subjected to affinity chromatography 204, typically involving Protein-A chromatography or other analogous chromatographic steps. The virus inactivation step 208 typically entails subjecting the feedstock to a low pH hold. One or more polishing chromatography steps 210 and 212 are performed to remove impurities, such as host cell proteins (HCP), DNA, charged variants, and aggregates. Cation exchange (CEX) chromatography is commonly used as an initial polishing chromatography step 210, but it may be accompanied by a second chromatography step 212 that either precedes or follows it. The second chromatography step 212 further removes host-cell-related impurities (e.g., HCP or DNA), or product related impurities such as aggregates. Anion exchange (AEX) chromatography and hydrophobic interaction chromatography (HIC) can be employed as second chromatography steps 212. Virus filtration 214 is performed to effect virus removal. Final purification steps 218 can include ultrafiltration and diafiltration, and preparation for formulation.

As generally described above, purification processes or DSP following the fermentation process can include (1) cell culture harvest, (2) chromatography (e.g., Protein-A chromatography and chromatographic polishing steps, including ion exchange and hydrophobic interaction chromatography), (3) viral inactivation, and (4) filtration (e.g., viral filtration, sterile filtration, dialysis, and ultrafiltration and diafiltration steps to concentrate the protein and exchange the protein into the formulation buffer). Examples are provided below to illustrate the advantages from using a viscosity-reducing excipient as described herein to improve process parameters associated with these purification processes. It is understood that the viscosity-reducing excipient or combinations thereof can be introduced at any phase of DSP by adding it to a carrier solution or in any other way engineering the contact of the protein of interest with the excipient, whether in soluble or stabilized form. In embodiments, a second viscosity-reducing compound can be added to the carrier solution during DSP, wherein the second viscosity-reducing compound adds an additional improvement to a particular parameter of interest.

(1) Cell Culture Harvest:

Cell culture harvest generally involves centrifugation and depth filtration operations in which cellular debris is physically removed from protein-containing solutions. The centrifugation step can provide a more complete separation of soluble protein from cell debris with the benefit of a viscosity-reducing excipient. Whether done by batch or continuous processing, the centrifuge separation requires the dense phase to consolidate as much as possible to maximize recovery of the target protein. In embodiments, addition of the above-identified excipients or combinations thereof can increase the process parameter of protein yield, for example, by increasing the yield of protein-containing centrate that flows away from the dense phase of the centrifuge separation process. The depth filtration step is a viscosity-limited step, and thus can be made more efficient by using an excipient that reduces solution viscosity. These processes can also introduce air bubbles into the protein solution, which can couple with shear-induced stresses to destabilize the therapeutic protein molecules being purified. Adding a viscosity-reducing excipient to the protein-containing solution, before and/or during cell culture harvest, as described above, can protect the protein from these stresses, thereby improving the process parameter of quantified product recovery.

(2) Chromatography:

After cell culture harvest by centrifugation or filtration, chromatography is typically used to separate the therapeutic protein from the fermentation broth. Protein A chromatography is used when the therapeutic protein is an antibody: Protein A is selective towards IgG antibodies, which it will bind dynamically at a high flow rate and capacity. Cation exchange (CEX) chromatography can be used as a cost-effective alternative to Protein A chromatography. If CEX is used, the pH of the feed must be adjusted and its conductivity decreased prior to loading onto the column to optimize the dynamic binding capacity. Mimetic resins can also be used as an alternative to Protein A chromatography. These resins provide ligands to bind immunoglobulins, for example Ig-binding proteins like protein G or protein L, synthetic ligands, or protein A-like porous polymers.

Other chromatography processes can be employed during DSP. Ion exchange chromatography (IEC) can be used to remove impurities introduced during previous processes, for example, leached Protein A, endotoxins or viruses from the cell line, remaining host cell proteins or DNA, or media components. IEC, whether CEX or anion exchange chromatography, can be applied directly after Protein A chromatography. Hydrophobic interaction chromatography (HIC) can complement IEC, generally used as a polishing step to remove aggregates. In embodiments, the use of the above-identified excipients can increase the solubility of, and decrease the viscosity of host cell proteins during chromatography column loading steps. In embodiments, the use of the above-identified excipients can increase the solubility of, and decrease the viscosity of the therapeutic protein during chromatography column loading steps and elution steps.

Chromatographic processes during protein purification impose harsh conditions on the protein formulation, such as (a) low pH conditions during elution from Protein-A chromatography columns, (b) elevated local protein concentration (often on the order of 300-400 mg/mL) within the pore-space of chromatographic resin, (c) elevated salt concentrations during ion exchange chromatography, and (d) elevated concentrations of salting-out agents during elution from HIC columns. Adding a viscosity-reducing excipient to the protein-containing solution, before and/or during chromatography, as described above, can facilitate the transit of the proteins through the chromatography column so that they are less exposed to the potentially damaging conditions imposed by chromatographic processing steps. In addition, the elevated local protein concentration within the column pore-space can result in a highly viscous material within this space, which places significant back pressure on the column. To alleviate this back pressure, media with relatively large pores are typically used. However, the resolving power of large-pore media is lower than small-pore counterparts. The incorporation of viscosity-modifying excipients as described above can enable the use of smaller pores in the chromatographic media. In embodiments, the elution steps from Protein-A chromatography expose the therapeutic protein to a low pH condition that can reduce solubility and increase aggregation of the target protein; addition of the excipients can increase the solubility of the target protein such that recovery yield from the Protein-A chromatography step is improved. In other embodiments, use of the excipient can enable elution of the target protein from Protein-A resin at a higher pH, and this can reduce chemical stresses on the target protein, resulting in improving a process parameter of protein yield by reducing the amount of protein degradation during processing.

(3) Viral Inactivation:

Viral inactivation processes typically involve holding the protein solution at a low pH, e.g., pH lower than 4, for an extended period of time. This environment, though, can destabilize therapeutic proteins. Formulating the protein in the presence of a viscosity-reducing excipient, for example, by adding a viscosity-reducing excipient before and/or during a viral inactivation process, can improve process parameters such as the stability or solubility of the protein, or its net yield.

(4) Filtration:

Filtration processes include viral filtration processes (nanofiltration) to remove virus particles, and ultrafiltration/diafiltration processes to concentrate protein solutions and to exchange buffer systems.

(a) Viral filtration purifies the protein solution by removing virus particles, which can be on the order of twice the size of a recombinant human monoclonal antibodies. Thus, the filtration membrane for viral filtration can require nano-sized pores. As a result of the small pore size through which the proteins must pass, this filtration step can introduce stress to the protein, and is accompanied by significant levels of membrane fouling from protein aggregate particles. The addition of a viscosity-reducing excipient, for example, before and/or during filtration, as described above, can reduce a measurable parameter such as back pressure in the filtration system by increasing collective diffusivity, and can decrease the tendency for membrane fouling by mitigating the protein-protein interactions that give rise to it. The end result is improvement in those parameters indicting improved performance of the viral filtration unit during protein purification.

(b) Ultrafiltration and diafiltration (UF/DF) processes concentrate protein solutions and exchange buffer systems by passing the protein-containing solution through a filter membrane with a characteristic molecular weight cutoff that is smaller than the protein of interest. In this step, the protein solution faces high shear stresses within the filter units, elevated protein concentrations, and adsorption of the protein to the hydrophobic membranes typically used during UF/DF processes, all of which can increase protein aggregation. The addition of a viscosity-reducing excipient, for example, before and/or during a UF/DF process, as described above, can reduce back pressure in the filtration system by increasing collective diffusivity (measured, for example, by an increase in kr)). This not only reduces shear stress across the membrane, but also promotes back-diffusion away from the filter membrane, thus lowering the effective protein concentration at the membrane interface and increasing the permeate flux. As a result, the use of viscosity-reducing excipients can improve parameters associated with higher throughput during these filtration processes, with reduced product losses and increased net yield. Additionally, passing viscous fluids through ultra- and diafilters can produce a large pressure drop across the filter device, making the separation inefficient. Formulating the protein solution in the presence of viscosity-reducing excipients as described above can substantially reduce the pressure drop across the filter device, thereby improving the process parameters of operation costs and processing time by decreasing them both.

After the upstream protein processing or downstream purification have been completed with the added excipient, the excipient can remain as a part of the drug substance mixture or it can be separated from the protein active ingredient. Typical small molecule separation methods can be used to separate the excipient from the protein active ingredient, such as buffer exchange, ion exchange, ultrafiltration, and dialysis. In addition to the beneficial effects on the protein purification processes as outlined above, the use of the above-identified excipients can protect and preserve equipment used in protein manufacture, processing, and purification. For example, equipment-related processes such as the cleanup, sterilization, and maintenance of protein processing equipment can be facilitated by the use of the above-identified excipients due to decreased fouling, decreased denaturing, lower viscosity, and improved solubility of the protein, and parameters associated with the improvement of these processes are similarly improved.

While the use of an excipient compound to improve upstream and/or downstream processing has been described extensively herein, it is understood that a combination of excipients can be added together in order to achieve a desired effect, such as an improvement in a parameter of interest. The term "excipient additive" can refer to either a single excipient compound that leads to the desired effect or improved parameter, or to a combination of excipient compounds where the combination is responsible for the desired effect or the improved parameter.

EXAMPLES

Materials:
Bovine gamma globulin (BGG), >99% purity, Catalog #G5009, Sigma Aldrich
Histidine, Sigma Aldrich
Other materials described in the examples below were from Sigma Aldrich unless otherwise specified.

Example 1: Preparation of Formulations Containing Excipient Compounds and Test Protein Formulations were prepared using an excipient compound and a test protein, where the test protein was intended to simulate either a therapeutic protein that would be used in a therapeutic formulation, or a non-therapeutic protein that would be used in a non-therapeutic formulation. Such formulations were prepared in 50 mM histidine hydrochloride with different excipient compounds for viscosity measurement in the following way. Histidine hydrochloride was first prepared by dissolving 1.94 g histidine in distilled water and adjusting the pH to about 6.0 with 1 M hydrochloric acid (Sigma-Aldrich, St. Louis, Mo.) and then diluting to a final volume of 250 mL with distilled water in a volumetric flask. Excipient compounds were then dissolved in 50 mM histidine HCl. Lists of excipients are provided below in Examples 4, 5, 6, and 7. In some cases excipient compounds were adjusted to pH 6 prior to dissolving in 50 mM histidine HCl. In this case the excipient compounds were first dissolved in deionized water at about 5 wt % and the pH was adjusted to about 6.0 with either hydrochloric acid or sodium hydroxide. The prepared salt solution was then placed in a convection laboratory oven at about 65° C. to evaporate the water and isolate the solid excipient. Once excipient solutions in 50 mM histidine HCl had been prepared, the test protein bovine gamma globulin (BGG) was dissolved at a ratio of about 0.336 g BGG per 1 mL excipient solution. This resulted in a final protein concentration of about 280 mg/mL. Solutions of BGG in 50 mM histidine HCl with excipient were formulated in 20 mL vials and allowed to shake at 100 rpm on an orbital shaker table overnight. BGG solutions were then transferred to 2 mL microcentrifuge tubes and centrifuged for ten minutes at 2300 rpm in an IEC Micro-Max microcentrifuge to remove entrained air prior to viscosity measurement.

Example 2: Viscosity Measurement

Viscosity measurements of formulations prepared as described in Example 1 were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty-second measurement collection period. The three data points collected were then averaged and recorded as the viscosity for the sample.

Example 3: Protein Concentration Measurement

The concentration of the protein in the experimental solutions was determined by measuring the optical absorbance of the protein solution at a wavelength of 280 nm in a UV/VIS Spectrometer (Perkin Elmer Lambda 35). First the instrument was calibrated to zero absorbance with a 50 mM histidine buffer at pH 6. Next the protein solutions were diluted by a factor of 300 with the same histidine buffer and the absorbance at 280 nm recorded. The final concentration of the protein in the solution was calculated by using the extinction coefficient value of 1.264 mL/(mg×cm).

Example 4: Formulations with Hindered Amine Excipient Compounds

Formulations containing 280 mg/mL BGG were prepared as described in Example 1, with some samples containing added excipient compounds. In these tests, the hydrochloride salts of dimethylcyclohexylamine (DMCHA), dicyclohexylmethylamine (DCHMA), dimethylaminopropylamine (DMAPA), triethanolamine (TEA), dimethylethanolamine (DMEA), and niacinamide were tested as examples of the hindered amine excipient compounds. Also, a hydroxybenzoic acid salt of DMCHA and a taurine-dicyandiamide adduct were tested as examples of the hindered amine excipient compounds. The viscosity of each protein solution was measured as described in Example 2, and the results are presented in Table 1 below, showing the benefit of the added excipient compounds in reducing viscosity.

TABLE 1

| Test Number | Excipient Added | Excipient Concentration (mg/mL) | Viscosity (cP) | Viscosity Reduction |
| --- | --- | --- | --- | --- |
| 4.1 | None | 0 | 79 | 0% |
| 4.2 | DMCHA-HCl | 28 | 50 | 37% |
| 4.3 | DMCHA-HCl | 41 | 43 | 46% |
| 4.4 | DMCHA-HCl | 50 | 45 | 43% |
| 4.5 | DMCHA-HCl | 82 | 36 | 54% |
| 4.6 | DMCHA-HCl | 123 | 35 | 56% |
| 4.7 | DMCHA-HCl | 164 | 40 | 49% |
| 4.8 | DMAPA-HCl | 87 | 57 | 28% |
| 4.9 | DMAPA-HCl | 40 | 54 | 32% |
| 4.10 | DCHMA-HCl | 29 | 51 | 35% |
| 4.11 | DCHMA-HCl | 50 | 51 | 35% |
| 4.14 | TEA-HCl | 97 | 51 | 35% |
| 4.15 | TEA-HCl | 38 | 57 | 28% |
| 4.16 | DMEA-HCl | 51 | 51 | 35% |
| 4.17 | DMEA-HCl | 98 | 47 | 41% |
| 4.20 | DMCHA-hydroxybenzoate | 67 | 46 | 42% |

TABLE 1-continued

| Test Number | Excipient Added | Excipient Concentration (mg/mL) | Viscosity (cP) | Viscosity Reduction |
|---|---|---|---|---|
| 4.21 | DMCHA-hydroxybenzoate | 92 | 42 | 47% |
| 4.22 | Product of Example 8 | 26 | 58 | 27% |
| 4.23 | Product of Example 8 | 58 | 50 | 37% |
| 4.24 | Product of Example 8 | 76 | 49 | 38% |
| 4.25 | Product of Example 8 | 103 | 46 | 42% |
| 4.26 | Product of Example 8 | 129 | 47 | 41% |
| 4.27 | Product of Example 8 | 159 | 42 | 47% |
| 4.28 | Product of Example 8 | 163 | 42 | 47% |
| 4.29 | Niacinamide | 48 | 39 | 51% |
| 4.30 | N-Methyl-2-pyrrolidone | 30 | 45 | 43% |
| 4.31 | N-Methyl-2-pyrrolidone | 52 | 52 | 34% |

Example 5: Formulations with Anionic Aromatic Excipient Compounds

Formulations of 280 mg/mL BGG were prepared as described in Example 1, with some samples containing added excipient compounds. The viscosity of each solution was measured as described in Example 2, and the results are presented in Table 2 below, showing the benefit of the added excipient compounds in reducing viscosity.

TABLE 2

| Test Number | Excipient Added | Excipient Concentration (mg/mL) | Viscosity (cP) | Viscosity Reduction |
|---|---|---|---|---|
| 5.1 | None | 0 | 79 | 0% |
| 5.2 | Sodium aminobenzoate | 43 | 48 | 39% |
| 5.3 | Sodium hydroxybenzoate | 26 | 50 | 37% |
| 5.4 | Sodium sulfanilate | 44 | 49 | 38% |
| 5.5 | Sodium sulfanilate | 96 | 42 | 47% |
| 5.6 | Sodium indole acetate | 52 | 58 | 27% |
| 5.7 | Sodium indole acetate | 27 | 78 | 1% |
| 5.8 | Vanillic acid, sodium salt | 25 | 56 | 29% |
| 5.9 | Vanillic acid, sodium salt | 50 | 50 | 37% |
| 5.10 | Sodium salicylate | 25 | 57 | 28% |
| 5.11 | Sodium salicylate | 50 | 52 | 34% |
| 5.12 | Adenosine monophosphate | 26 | 47 | 41% |
| 5.13 | Adenosine monophosphate | 50 | 66 | 16% |
| 5.14 | Sodium benzoate | 31 | 61 | 23% |
| 5.15 | Sodium benzoate | 56 | 62 | 22% |

Example 6: Formulations with Oligopeptide Excipient Compounds

Oligopeptides (n=5) were synthesized by NeoBioLab Inc. (Woburn, Mass.) in >95% purity with the N terminus as a free amine and the C terminus as a free acid. Dipeptides (n=2) were synthesized by LifeTein LLC (Somerset, N.J.) in 95% purity. Formulations of 280 mg/mL BGG were prepared as described in Example 1, with some samples containing the synthetic oligopeptides as added excipient compounds. The viscosity of each solution was measured as described in Example 2, and the results are presented in Table 3 below, showing the benefit of the added excipient compounds in reducing viscosity.

TABLE 3

| Test Number | Excipient Added | Excipient Concentration (mg/mL) | Viscosity (cP) | Viscosity Reduction |
|---|---|---|---|---|
| 6.1 | None | 0 | 79 | 0% |
| 6.2 | ArgX5 | 100 | 55 | 30% |
| 6.3 | ArgX5 | 50 | 54 | 32% |
| 6.4 | HisX5 | 100 | 62 | 22% |
| 6.5 | HisX5 | 50 | 51 | 35% |
| 6.6 | HisX5 | 25 | 60 | 24% |
| 6.7 | Trp2Lys3 | 100 | 59 | 25% |
| 6.8 | Trp2Lys3 | 50 | 60 | 24% |
| 6.9 | AspX5 | 100 | 102 | −29% |
| 6.10 | AspX5 | 50 | 82 | −4% |
| 6.11 | Dipeptide LE (Leu-Glu) | 50 | 72 | 9% |
| 6.12 | Dipeptide YE (Tyr-Glu) | 50 | 55 | 30% |
| 6.13 | Dipeptide RP (Arg-Pro) | 50 | 51 | 35% |
| 6.14 | Dipeptide RK (Arg-Lys) | 50 | 53 | 33% |
| 6.15 | Dipeptide RH (Arg-His) | 50 | 52 | 34% |
| 6.16 | Dipeptide RR (Arg-Arg) | 50 | 57 | 28% |
| 6.17 | Dipeptide RE (Arg-Glu) | 50 | 50 | 37% |
| 6.18 | Dipeptide LE (Leu-Glu) | 100 | 87 | −10% |
| 6.19 | Dipeptide YE (Tyr-Glu) | 100 | 68 | 14% |
| 6.20 | Dipeptide RP (Arg-Pro) | 100 | 53 | 33% |
| 6.21 | Dipeptide RK (Arg-Lys) | 100 | 64 | 19% |
| 6.22 | Dipeptide RH (Arg-His) | 100 | 72 | 9% |
| 6.23 | Dipeptide RR (Arg-Arg) | 100 | 62 | 22% |
| 6.24 | Dipeptide RE (Arg-Glu) | 100 | 66 | 16% |

Example 8: Synthesis of Guanyl Taurine Excipient

Guanyl taurine was prepared following method described in U.S. Pat. No. 2,230,965. Taurine (Sigma-Aldrich, St. Louis, Mo.) 3.53 parts were mixed with 1.42 parts of dicyandiamide (Sigma-Aldrich, St. Louis, Mo.) and grinded in a mortar and pestle until a homogeneous mixture was obtained. Next the mixture was placed in a flask and heated at 200° C. for 4 hours. The product was used without further purification.

Example 9: Protein Formulations Containing Excipient Compounds

Formulations were prepared using an excipient compound and a test protein, where the test protein was intended to simulate either a therapeutic protein that would be used in a therapeutic formulation, or a non-therapeutic protein that would be used in a non-therapeutic formulation. Such formulations were prepared in 50 mM aqueous histidine hydrochloride buffer solution with different excipient compounds for viscosity measurement in the following way. Histidine hydrochloride buffer solution was first prepared by dissolving 1.94 g histidine in distilled water and adjusting the pH to about 6.0 with 1 M hydrochloric acid (Sigma-Aldrich, St. Louis, Mo.) and then diluting to a final volume of 250 mL with distilled water in a volumetric flask. Excipient compounds were then dissolved in the 50 mM histidine HCl buffer solution. A list of the excipient compounds is provided in Table 4. In some cases, excipient compounds were dissolved in 50 mM histidine HCl buffer solution and the resulting solution pH was adjusted with small amounts of sodium hydroxide or hydrochloric acid to achieve pH 6 prior to dissolution of the model protein. In some cases, excipient compounds were adjusted to pH 6 prior to dissolving in 50 mM histidine HCl. In this case the excipient compounds were first dissolved in deionized water at about 5 wt % and the pH was adjusted to about 6.0 with either hydrochloric acid or sodium hydroxide. The prepared salt solution was then placed in a convection laboratory oven at about 65° C. to evaporate the water and isolate the solid excipient. Once excipient solutions in 50 mM histidine HCl had been prepared, the test protein, bovine gamma globulin (BGG) was dissolved at a ratio to achieve a final protein concentration of about 280 mg/mL. Solutions of BGG in 50 mM histidine HCl with excipient were formulated in 20 mL vials and allowed to shake at 100 rpm on an orbital shaker table overnight. BGG solutions were then transferred to 2 mL microcentrifuge tubes and centrifuged for ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty-second measurement collection period. The three data points collected were then averaged and recorded as the viscosity for the sample. Viscosities of solutions with excipient were normalized to the viscosity of the model protein solution without excipient. The normalized viscosity is the ratio of the viscosity of the model protein solution with excipient to the viscosity of the model protein solution with no excipient.

TABLE 4

| Test Number | Excipient Added | Excipient Concentration (mg/mL) | Normalized Viscosity (cP) | Viscosity Reduction |
|---|---|---|---|---|
| 9.1 | DMCHA-HCl | 120 | 0.44 | 56% |
| 9.2 | Niacinamide | 50 | 0.51 | 49% |
| 9.3 | Isonicotinamide | 50 | 0.48 | 52% |
| 9.4 | Tyramine HCl | 70 | 0.41 | 59% |
| 9.5 | Histamine HCl | 50 | 0.41 | 59% |
| 9.6 | Imidazole HCl | 100 | 0.43 | 57% |
| 9.7 | 2-methyl-2-imidazoline HCl | 60 | 0.43 | 57% |
| 9.8 | 1-butyl-3-methyl-imidazolium chloride | 100 | 0.48 | 52% |
| 9.9 | Procaine HCl | 50 | 0.53 | 47% |
| 9.10 | 3-aminopyridine | 50 | 0.51 | 49% |
| 9.11 | 2,4,6-trimethyl-pyridine | 50 | 0.49 | 51% |
| 9.12 | 3-pyridine methanol | 50 | 0.53 | 47% |
| 9.13 | Nicotinamide adenine dinucleotide | 20 | 0.56 | 44% |
| 9.15 | Sodium phenylpyruvate | 55 | 0.57 | 43% |
| 9.16 | 2-Pyrrolidinone | 60 | 0.68 | 32% |
| 9.17 | Morpholine HCl | 50 | 0.60 | 40% |
| 9.18 | Agmatine sulfate | 55 | 0.77 | 23% |
| 9.19 | 1-butyl-3-methyl-imidazolium iodide | 60 | 0.66 | 34% |
| 9.21 | L-Anserine nitrate | 50 | 0.79 | 21% |
| 9.22 | 1-hexyl-3-methyl-imidazolium chloride | 65 | 0.89 | 11% |
| 9.23 | N,N-diethyl nicotinamide | 50 | 0.67 | 33% |
| 9.24 | Nicotinic acid, sodium salt | 100 | 0.54 | 46% |
| 9.25 | Biotin | 20 | 0.69 | 31% |

Example 10: Preparation of Formulations Containing Excipient Combinations and Test Protein Formulations were prepared using a primary excipient compound, a secondary excipient compound and a test protein, where the test protein was intended to simulate either a therapeutic protein that would be used in a therapeutic formulation, or a non-therapeutic protein that would be used in a non-therapeutic formulation. The primary excipient compounds were selected from compounds having both anionic and aromatic functionality, as listed below in Table 5. The secondary excipient compounds were selected from compounds having either nonionic or cationic charge at pH 6 and either imidazoline or benzene rings, as listed below in Table 5. Formulations of these excipients were prepared in 50 mM histidine hydrochloride buffer solution for viscosity measurement in the following way. Histidine hydrochloride was first prepared by dissolving 1.94 g histidine in distilled water and adjusting the pH to about 6.0 with 1 M hydrochloric acid (Sigma-Aldrich, St. Louis, Mo.) and then diluting to a final volume of 250 mL with distilled water in a volumetric flask. The individual primary or secondary excipient compounds were then dissolved in 50 mM histidine HCl. Combinations of primary and secondary excipients were dissolved in 50 mM histidine HCl and the resulting solution pH adjusted with small amounts of sodium hydroxide or hydrochloric acid to achieve pH 6 prior to dissolution of the model protein. Once excipient solutions had been prepared as described above, the test protein bovine gamma globulin (BGG) was dissolved into each test solution at a ratio to achieve a final protein concentration of about 280 mg/mL. Solutions of BGG in 50 mM histidine HCl with excipient were formulated in 20 mL vials and allowed to shake at 100 rpm on an orbital shaker table overnight. BGG solutions were then transferred to 2 mL microcentrifuge tubes and centrifuged for ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and a subsequent twenty-second measurement collection period. The three data points collected were then averaged and recorded as the viscosity for the sample. Viscosities of solutions with excipient were normalized to the viscosity of the model protein solution without excipient, and summarized in Table 5 below. The normalized viscosity is the ratio of the viscosity of the model protein solution with excipient to the viscosity of the model protein solution with no excipient. The example shows that a combination of primary and secondary excipients can give a better result than a single excipient.

TABLE 5

| | Primary Excipient | | Secondary Excipient | | |
|---|---|---|---|---|---|
| Test Number | Name | Concentration (mg/mL) | Name | Concentration (mg/mL) | Normalized Viscosity |
| 10.1 | Salicylic Acid | 30 | None | 0 | 0.79 |
| 10.2 | Salicylic Acid | 25 | Imidazole | 4 | 0.59 |
| 10.3 | 4-hydroxybenzoic acid | 30 | None | 0 | 0.61 |
| 10.4 | 4-hydroxybenzoic acid | 25 | Imidazole | 5 | 0.57 |
| 10.5 | 4-hydroxybenzene sulfonic acid | 31 | None | 0 | 0.59 |
| 10.6 | 4-hydroxybenzene sulfonic acid | 26 | Imidazole | 5 | 0.70 |
| 10.7 | 4-hydroxybenzene sulfonic acid | 25 | Caffeine | 5 | 0.69 |
| 10.8 | None | 0 | Caffeine | 10 | 0.73 |
| 10.9 | None | 0 | Imidazole | 5 | 0.75 |

Example 11: Preparation of Formulations Containing Excipient Combinations and Test Protein Formulations were prepared using a primary excipient compound, a secondary excipient compound and a test protein, where the test protein was intended to simulate a therapeutic protein that would be used in a therapeutic formulation, or a non-therapeutic protein that would be used in a non-therapeutic formulation. The primary excipient compounds were selected from compounds having both anionic and aromatic functionality, as listed below in Table 6. The secondary excipient compounds were selected from compounds having either nonionic or cationic charge at pH 6 and either imidazoline or benzene rings, as listed below in Table 6. Formulations of these excipients were prepared in distilled water for viscosity measurement in the following way. Combinations of primary and secondary excipients were dissolved in distilled water and the resulting solution pH adjusted with small amounts of sodium hydroxide or hydrochloric acid to achieve pH 6 prior to dissolution of the model protein. Once excipient solutions in distilled water had been prepared, the test protein bovine gamma globulin (BGG) was dissolved at a ratio to achieve a final protein concentration of about 280 mg/mL. Solutions of BGG in distilled water with excipient were formulated in 20 mL vials and allowed to shake at 100 rpm on an orbital shaker table overnight. BGG solutions were then transferred to 2 mL microcentrifuge tubes and centrifuged for ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and a subsequent twenty-second measurement collection period.

The three data points collected were then averaged and recorded as the viscosity for the sample. Viscosities of solutions with excipient were normalized to the viscosity of the model protein solution without excipient, and summarized in Table 6 below. The normalized viscosity is the ratio of the viscosity of the model protein solution with excipient to the viscosity of the model protein solution with no excipient. The example shows that a combination of primary and secondary excipients can give a better result than a single excipient.

TABLE 6

| | Primary Excipient | | Secondary Excipient | | |
|---|---|---|---|---|---|
| Test Number | Name | Concentration (mg/mL) | Name | Concentration (mg/mL) | Normalized Viscosity |
| 11.1 | Salicylic Acid | 20 | None | 0 | 0.96 |
| 11.2 | Salicylic Acid | 20 | Caffeine | 5 | 0.71 |
| 11.3 | Salicylic Acid | 20 | Niacinamide | 5 | 0.76 |
| 11.4 | Salicylic Acid | 20 | Imidazole | 5 | 0.73 |

Example 12: Preparation of Formulations Containing Excipient Compounds and PEG

Materials: All materials were purchased from Sigma-Aldrich, St. Louis, Mo. Formulations were prepared using an excipient compound and PEG, where the PEG was intended to simulate a therapeutic PEGylated protein that would be used in a therapeutic formulation. Such formulations were prepared by mixing equal volumes of a solution of PEG with a solution of the excipient. Both solutions were prepared in a Tris buffer consisting of 10 mM Tris, 135 mM NaCl, 1 mM trans-cinnamic acid at pH of 7.3.

The PEG solution was prepared by mixing 3 g of poly (ethylene oxide) average Mw ~1,000,000 (Aldrich Catalog #372781) with 97 g of the Tris buffer solution. The mixture was stirred overnight for complete dissolution.

An example of the excipient solution preparation is as follows: An approximately 80 mg/mL solution of citric acid in the Tris buffer was prepared by dissolving 0.4 g of citric acid (Aldrich cat. #251275) in 5 mL of the Tris buffer solution and adjusted the pH to 7.3 with minimum amount of 10 M NaOH solution.

The PEG excipient solution was prepared by mixing 0.5 mL of the PEG solution with 0.5 mL of the excipient solution and mixed by using a vortex for a few seconds. A control sample was prepared by mixing 0.5 mL of the PEG solution with 0.5 mL of the Tris buffer solution.

Example 13: Viscosity Measurements of Formulations Containing Excipient Compounds and PEG Viscosity measurements of the formulations prepared were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample.

The results presented in Table 7 show the effect of the added excipient compounds in reducing viscosity.

TABLE 7

| Test Number | Excipient | Excipient Concentration (mg/mL) | Viscosity (cP) | Viscosity Reduction |
| --- | --- | --- | --- | --- |
| 13.1 | None | 0 | 104.8 | 0% |
| 13.2 | Citric acid Na salt | 40 | 56.8 | 44% |
| 13.3 | Citric acid Na salt | 20 | 73.3 | 28% |
| 13.4 | glycerol phosphate | 40 | 71.7 | 30% |
| 13.5 | glycerol phosphate | 20 | 83.9 | 18% |
| 13.6 | Ethylene diamine | 40 | 84.7 | 17% |
| 13.7 | Ethylene diamine | 20 | 83.9 | 15% |
| 13.8 | EDTA/K salt | 40 | 67.1 | 36% |
| 13.9 | EDTA/K salt | 20 | 76.9 | 27% |
| 13.10 | EDTA/Na salt | 40 | 68.1 | 35% |
| 13.11 | EDTA/Na salt | 20 | 77.4 | 26% |
| 13.12 | D-Gluconic acid/K salt | 40 | 80.32 | 23% |
| 13.13 | D-Gluconic acid/K salt | 20 | 88.4 | 16% |
| 13.14 | D-Gluconic acid/Na salt | 40 | 81.24 | 23% |
| 13.15 | D-Gluconic acid/Na salt | 20 | 86.6 | 17% |
| 13.16 | lactic acid/K salt | 40 | 80.42 | 23% |
| 13.17 | lactic acid/K salt | 20 | 85.1 | 19% |
| 13.18 | lactic acid/Na salt | 40 | 86.55 | 17% |
| 13.19 | lactic acid/Na salt | 20 | 87.2 | 17% |
| 13.20 | etidronic acid/K salt | 24 | 71.91 | 31% |
| 13.21 | etidronic acid/K salt | 12 | 80.5 | 23% |
| 13.22 | etidronic acid/Na salt | 24 | 71.6 | 32% |
| 13.23 | etidronic acid/Na salt | 12 | 79.4 | 24% |

Example 14: Preparation of PEGylated BSA with 1 PEG Chain Per BSA Molecule

To a beaker was added 200 mL of a phosphate buffered saline (Aldrich Cat. #P4417) and 4 g of BSA (Aldrich Cat. #A7906) and mixed with a magnetic bar. Next 400 mg of methoxy polyethylene glycol maleimide, MW=5,000, (Aldrich Cat. #63187) was added. The reaction mixture was allowed to react overnight at room temperature. The following day, 20 drops of HCl 0.1 M were added to stop the reaction. The reaction product was characterized by SDS-Page and SEC which clearly showed the PEGylated BSA. The reaction mixture was placed in an Amicon centrifuge tube with a molecular weight cutoff (MWCO) of 30,000 and concentrated to a few milliliters. Next the sample was diluted 20 times with a histidine buffer, 50 mM at a pH of approximately 6, followed by concentrating until a high viscosity fluid was obtained. The final concentration of the protein solution was obtained by measuring the absorbance at 280 nm and using a coefficient of extinction for the BSA of 0.6678. The results indicated that the final concentration of BSA in the solution was 342 mg/mL.

Example 15: Preparation of PEGylated BSA with Multiple PEG Chains Per BSA Molecule A 5 mg/mL solution of BSA (Aldrich A7906) in phosphate buffer, 25 mM at pH of 7.2, was prepared by mixing 0.5 g of the BSA with 100 mL of the buffer. Next 1 g of a methoxy PEG propionaldehyde Mw=20,000 (JenKem Technology, Plano, Tex. 75024) was added followed by 0.12 g of sodium cyanoborohydride (Aldrich 156159). The reaction was allowed to proceed overnight at room temperature. The following day the reaction mixture was diluted 13 times with a Tris buffer (10 mM Tris, 135 mM NaCl at pH=7.3) and concentrated using Amicon centrifuge tubes MWCO of 30,000 until a concentration of approximately 150 mg/mL was reached.

Example 16: Preparation of PEGylated Lysozyme with Multiple PEG Chains Per Lysozyme Molecule A 5 mg/mL solution of lysozyme (Aldrich L6876) in phosphate buffer, 25 mM at pH of 7.2, was prepared by mixing 0.5 g of the lysozyme with 100 mL of the buffer. Next 1 g of a methoxy PEG propionaldehyde Mw=5,000 (JenKem Technology, Plano, Tex. 75024) was added followed by 0.12 g of sodium cyanoborohydride (Aldrich 156159). The reaction was allowed to proceed overnight at room temperature. The following day the reaction mixture was diluted 49 times with the phosphate buffer, 25 mM at pH of 7.2, and concentrated using Amicon centrifuge tubes MWCO of 30,000. The final concentration of the protein solution was obtained by measuring the absorbance at 280 nm and using a coefficient of extinction for the lysozyme of 2.63. The final concentration of lysozyme in the solution was 140 mg/mL.

Example 17: Effect of Excipients on Viscosity of PEGylated BSA with 1 PEG Chain Per BSA Molecule Formulations of PEGylated BSA (from Example 14 above) with excipients were prepared by adding 6 or 12 milligrams of the excipient salt to 0.3 mL of the PEGylated BSA solution. The solution was mixed by gently shaking and the viscosity was measured by a RheoSense microVisc equipped with an A10 channel (100-micron depth) at a shear rate of 500 sec−1. The viscometer measurements were completed at ambient temperature.

The results presented in Table 8 shows the effect of the added excipient compounds in reducing viscosity.

TABLE 8

| Test Number | Excipient | Excipient Concentration (mg/mL) | Viscosity (cP) | Viscosity Reduction |
| --- | --- | --- | --- | --- |
| 17.1 | None | 0 | 228.6 | 0% |
| 17.2 | Alpha-Cyclodextrin sulfated Na salt | 20 | 151.5 | 34% |
| 17.3 | K acetate | 40 | 89.5 | 60% |

Example 18: Effect of Excipients on Viscosity of PEGylated BSA with Multiple PEG Chains Per BSA Molecule A formulation of PEGylated BSA (from Example 15 above) with citric acid Na salt as excipient was prepared by adding 8 milligrams of the excipient salt to 0.2 mL of the PEGylated BSA solution. The solution was mixed by gently shaking and the viscosity was measured by a RheoSense microVisc equipped with an A10 channel (100 micron depth) at a shear rate of 500 sec−1. The viscometer measurements were completed at ambient temperature. The results presented in Table 9 shows the effect of the added excipient compounds in reducing viscosity.

TABLE 9

| Test Number | Excipient Added | Excipient Concentration (mg/mL) | Viscosity (cP) | Viscosity Reduction |
|---|---|---|---|---|
| 18.1 | None | 0 | 56.8 | 0% |
| 18.2 | Citric acid Na salt | 40 | 43.5 | 23% |

Example 19: Effect of Excipients on Viscosity of PEGylated Lysozyme with Multiple PEG Chains Per Lysozyme Molecule A formulation of PEGylated lysozyme (from Example 16 above) with potassium acetate as excipient was prepared by adding 6 milligrams of the excipient salt to 0.3 mL of the PEGylated lysozyme solution. The solution was mixed by gently shaking and the viscosity was measured by a RheoSense microVisc equipped with an A10 channel (100 micron depth) at a shear rate of 500 sec−1. The viscometer measurements were completed at ambient temperature. The results presented in the next table shows the benefit of the added excipient compounds in reducing viscosity.

TABLE 10

| Test Number | Excipient | Excipient Concentration (mg/mL) | Viscosity (cP) | Viscosity Reduction |
|---|---|---|---|---|
| 19.1 | None | 0 | 24.6 | 0% |
| 19.2 | K acetate | 20 | 22.6 | 8% |

Example 20: Protein Formulations Containing Excipient Combinations

Formulations were prepared using an excipient compound or a combination of two excipient compounds and a test protein, where the test protein was intended to simulate a therapeutic protein that would be used in a therapeutic formulation. These formulations were prepared in 20 mM histidine buffer with different excipient compounds for viscosity measurement in the following way. Excipient combinations were dissolved in 20 mM histidine and the resulting solution pH adjusted with small amounts of sodium hydroxide or hydrochloric acid to achieve pH 6 prior to dissolution of the model protein. Excipient compounds for this Example are listed below in Table 11. Once excipient solutions had been prepared, the test protein bovine gamma globulin (BGG) was dissolved at a ratio to achieve a final protein concentration of about 280 mg/mL. Solutions of BGG in the excipient solutions were formulated in 5 mL sterile polypropylene tubes and allowed to shake at 80-100 rpm on an orbital shaker table overnight. BGG solutions were then transferred to 2 mL microcentrifuge tubes and centrifuged for about ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample. Viscosities of solutions with excipient were normalized to the viscosity of the model protein solution without excipient, and the results are shown in Table 11 below. The normalized viscosity is the ratio of the viscosity of the model protein solution with excipient to the viscosity of the model protein solution with no excipient.

TABLE 11

| Test # | Excipient A Name | Conc. (mg/mL) | Excipient B Name | Conc. (mg/mL) | Normalized Viscosity |
|---|---|---|---|---|---|
| 20.1 | None | 0 | None | 0 | 1.00 |
| 20.2 | Aspartame | 10 | None | 0 | 0.83 |
| 20.3 | Saccharin | 60 | None | 0 | 0.51 |
| 20.4 | Acesulfame K | 80 | None | 0 | 0.44 |
| 20.5 | Theophylline | 10 | None | 0 | 0.84 |
| 20.6 | Saccharin | 30 | None | 0 | 0.58 |
| 20.7 | Acesulfame K | 40 | None | 0 | 0.61 |
| 20.8 | Caffeine | 15 | Taurine | 15 | 0.82 |
| 20.9 | Caffeine | 15 | Tyramine | 15 | 0.67 |

Example 21: Protein Formulations Containing Excipients to Reduce Viscosity and Injection Pain Formulations were prepared using an excipient compound, a second excipient compound, and a test protein, where the test protein was intended to simulate a therapeutic protein that would be used in a therapeutic formulation. The first excipient compound, Excipient A, was selected from a group of compounds having local anesthetic properties. The first excipient, Excipient A and the second excipient, Excipient B are listed in Table 12. These formulations were prepared in 20 mM histidine buffer using Excipient A and Excipient B in the following way, so that their viscosities could be measured. Excipients in the amounts disclosed in Table 12 were dissolved in 20 mM histidine and the resulting solutions were pH adjusted with small amounts of sodium hydroxide or hydrochloric acid to achieve pH 6 prior to dissolution of the model protein. Once excipient solutions had been prepared, the test protein bovine gamma globulin (BGG) was dissolved in the excipient solution at a ratio to achieve a final protein concentration of about 280 mg/mL. Solutions of BGG in the excipient solutions were formulated in 5 mL sterile polypropylene tubes and allowed to shake at 80-100 rpm on an orbital shaker table overnight. BGG-excipient solutions were then transferred to 2 mL microcentrifuge tubes and centrifuged for about ten minutes at 2300 rpm in an IEC MicroMax microcentrifuge to remove entrained air prior to viscosity measurement.

Viscosity measurements of the formulations prepared as described above were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample. Viscosities of solutions with excipient were normalized to the viscosity of the model protein solution without excipient, and the results are shown in Table 12 below. The normalized viscosity is the ratio of the viscosity of the model protein solution with excipient to the viscosity of the model protein solution with no excipient.

TABLE 12

| Test # | Excipient A Name | Conc. (mg/mL) | Excipient B Name | Conc. (mg/mL) | Normalized Viscosity |
|---|---|---|---|---|---|
| 21.1 | None | 0 | None | 0 | 1.00 |
| 21.2 | Lidocaine | 45 | None | 0 | 0.73 |
| 21.3 | Lidocaine | 23 | None | 0 | 0.74 |
| 21.4 | Lidocaine | 10 | Caffeine | 15 | 0.71 |
| 21.5 | Procaine HCl | 40 | None | 0 | 0.64 |
| 21.6 | Procaine HCl | 20 | Caffeine | 15 | 0.69 |

Example 22: Formulations Containing Excipient Compounds and PEG

Formulations were prepared using an excipient compound and PEG, where the PEG was intended to simulate a therapeutic PEGylated protein that would be used in a therapeutic formulation, and where the excipient compounds were provided in the amounts as listed in Table 13. These formulations were prepared by mixing equal volumes of a solution of PEG with a solution of the excipient. Both solutions were prepared in deionized (DI) Water.

The PEG solution was prepared by mixing 16.5 g of poly(ethylene oxide) average Mw ~100,000 (Aldrich Catalog #181986) with 83.5 g of DI water. The mixture was stirred overnight for complete dissolution.

The excipient solutions were prepared by this general method and as detailed in Table 13 below: An approximately 20 mg/mL solution of potassium phosphate tribasic (Aldrich Catalog #P5629) in DI water was prepared by dissolving 0.05 g of potassium phosphate in 5 mL of DI water. The PEG excipient solution was prepared by mixing 0.5 mL of the PEG solution with 0.5 mL of the excipient solution and mixed by using a vortex for a few seconds. A control sample was prepared by mixing 0.5 mL of the PEG solution with 0.5 mL of DI water. Viscosity was measured and results are recorded in Table 13 below.

TABLE 13

| Test Number | Excipient | Excipient Concentration (mg/mL) | Viscosity (cP) | Viscosity Reduction (%) |
|---|---|---|---|---|
| 22.1 | None | 0 | 79.7 | 0 |
| 22.2 | Citric acid Na salt | 10 | 74.9 | 6.0 |
| 22.3 | Potassium phosphate | 10 | 72.3 | 9.3 |
| 22.4 | Citric acid Na salt/ Potassium phosphate | 10/10 | 69.1 | 13.3 |
| 22.5 | Sodium sulfate | 10 | 75.1 | 5.8 |
| 22.6 | Citric acid Na salt/ Sodium sulfate | 10/10 | 70.4 | 11.7 |

Example 23: Improved Processing of Protein Solutions with Excipients

Two BGG solutions were prepared by mixing 0.25 g of solid BGG with 4 ml of a buffer solution. For Sample A: Buffer solution was 20 mM histidine buffer (pH=6.0). For sample B: Buffer solution was 20 mM histidine buffer containing 15 mg/ml of caffeine (pH=6). The dissolution of the solid BGG was carried out by placing the samples in an orbital shaker set at 100 rpm. The buffer sample containing caffeine excipient was observed to dissolve the protein faster. For the sample with the caffeine excipient (Sample B) complete dissolution of the BGG was achieved in 15 minutes. For the sample without the caffeine (Sample A) the dissolution needed 35 minutes.

Next the samples were placed in 2 separate Amicon Ultra 4 Centrifugal Filter Unit with a 30,000 molecular weight cut off and the samples were centrifuged at 2,500 rpm at 10 minutes intervals. The filtrate volume recovered after each 10 minute centrifuge run was recorded. The results in Table 14 show the faster recovery of the filtrate for Sample B. In addition, Sample B kept concentrating with every additional run but Sample A reached a maximum concentration point and further centrifugation did not result in further sample concentration.

TABLE 14

| Centrifuge time (min) | Sample A filtrate collected (mL) | Sample B filtrate collected (mL) |
|---|---|---|
| 10 | 0.28 | 0.28 |
| 20 | 0.56 | 0.61 |
| 30 | 0.78 | 0.88 |
| 40 | 0.99 | 1.09 |
| 50 | 1.27 | 1.42 |
| 60 | 1.51 | 1.71 |
| 70 | 1.64 | 1.99 |
| 80 | 1.79 | 2.29 |
| 90 | 1.79 | 2.39 |
| 100 | 1.79 | 2.49 |

Example 24: Protein Formulations Containing Multiple Excipients

This example shows how the combination of caffeine and arginine as excipients has a beneficial effect on decreasing viscosity of a BGG solution. Four BGG solutions were prepared by mixing 0.18 g of solid BGG with 0.5 mL of a 20 mM Histidine buffer at pH 6. Each buffer solution contained different excipient or combination of excipients as described in the table below. The viscosity of the solutions was measured as described in previous examples. The results show that the hindered amine excipient, caffeine, can be combined with known excipients such as arginine, and the combination has better viscosity reduction properties than the individual excipients by themselves.

TABLE 15

| Sample | Excipient added | Viscosity (cP) | Viscosity Reduction (%) |
|---|---|---|---|
| A | None | 130.6 | 0 |
| B | Caffeine (10 mg/ml) | 87.9 | 33 |
| C | Caffeine (10 mg/ml)/ Arginine (25 mg/ml) | 66.1 | 49 |
| D | Arginine (25 mg/ml) | 76.7 | 41 |

Arginine was added to 280 mg/mL solutions of BGG in histidine buffer at pH 6. At levels above 50 mg/mL, adding more arginine did not decrease viscosity further, as shown in Table 16.

TABLE 16

| Arginine added (mg/mL) | Viscosity (cP) | Viscosity reduction (%) |
| --- | --- | --- |
| 0 | 79.0 | 0% |
| 53 | 40.9 | 48% |
| 79 | 46.1 | 42% |
| 105 | 47.8 | 40% |
| 132 | 49.0 | 38% |
| 158 | 48.0 | 39% |
| 174 | 50.3 | 36% |
| 211 | 51.4 | 35% |

Caffeine was added to 280 mg/mL solutions of BGG in histidine buffer at pH 6. At levels above 10 mg/ml, adding more caffeine did not decrease viscosity further, as shown in Table 17.

TABLE 17

| Caffeine added (mg/mL) | Viscosity (cP) | Viscosity reduction (%) |
| --- | --- | --- |
| 0 | 79 | 0% |
| 10 | 60 | 31% |
| 15 | 62 | 23% |
| 22 | 50 | 45% |

Example 25: Caffeine Effect During TFF Concentration Process

In this Example, bovine gamma globulin (BGG) solutions were concentrated in the presence and absence of caffeine using tangential flow filtration (TFF). The Labscale TFF System, produced by EMD Millipore (Billerica, Mass.) was used to perform the experiments. The system was fitted with a Pellicon XL TFF cassette that contained an Ultracel membrane with 30 kDa molecular weight cutoff (EMD Millipore, Billerica, Mass.). The nominal membrane surface area was 50 cm². The feed pressure to the cassette was maintained at 30 psi while the retentate pressure was maintained at 10 psi. The filtrate flux was monitored over the course of the experiment by measuring its mass as a function of time. Approximately 12 grams of BGG were dissolved into 500 mL of buffer containing 15 mg/mL caffeine, 150 mM NaCl, and 20 mM histidine, adjusted to pH 6. A control sample was prepared by dissolving 12 grams of BGG into 500 mL of buffer containing 150 mM NaCl, and 20 mM histidine, adjusted to pH 6. The buffer components were purchased from Sigma-Aldrich. Both solutions were filtered through a 0.2 μm PES filter (VWR, Radnor, Pa.) prior to TFF processing. The performance of the test sample and control sample during TFF were measured by the mass transfer coefficient. The mass transfer coefficient was determined for each sample using the following equation (as described in J. Hung, A. U. Borwankar, B. J. Dear, T. M. Truskett, K. P. Johnston, High concentration tangential flow ultrafiltration of stable monoclonal antibody solutions with low viscosities. J. Memb. Sci. 508, 113-126 (2016)):

$$J = k_c \ln(C_w/C_b) \quad \text{(Eq. 3)}$$

Eq. 3 describes the filtrate flux J, where $k_c$ is the mass transfer coefficient, $C_w$ is the protein concentration in the vicinity of the membrane, and $C_b$ is the concentration in the liquid bulk, and Eq. 3 thereby permits calculation of the mass transfer coefficient L. A graph of the calculated flux J against the $\ln(C_b)$ yields a linear plot with slope of $-k_c$. Here the flux J is calculated by taking the derivative of the filtrate mass with respect to time and $C_b$ is calculated using a mass-balance. The best-fit mass transfer coefficients are listed in Table 18. The introduction of 15 mg/mL caffeine increased the value of the mass transfer coefficient by ~13%, from 22.5 to 25.4 $Lm^{-2} hr^{-1}$ (LMH).

TABLE 18

| Sample | Mass Transfer Coefficient $k_c$ (LMH) |
| --- | --- |
| Control | 22.5 ± 0.1 |
| 15 mg/mL caffeine | 25.4 ± 0.1 |

Example 26: Caffeine Effect During TFF Concentration Process

In this Example, bovine gamma globulin (BGG) solutions were concentrated in the presence and absence of caffeine using tangential flow filtration (TFF). The Labscale TFF System, produced by EMD Millipore (Billerica, Mass.) was used to perform the experiments. The system was fitted with a Pellicon XL TFF cassette that contained an Ultracel membrane with 30 kDa molecular weight cutoff (EMD Millipore, Billerica, Mass.). The nominal membrane surface area was 50 cm². A control sample was prepared by dissolving 14.6 grams of BGG into 582 mL of buffer containing 150 mM NaCl, and 20 mM histidine, adjusted to pH 6, such that the initial BGG concentration was nominally 25.1 mg/mL. The material was filtered through a 0.2 μm PES filter (VWR, Radnor, Pa.) and then processed in the TFF device. The pump speed was adjusted such that the feed pressure was initially 30 psi and the retentate valve was adjusted such that the retentate pressure was initially 10 psi. The material was concentrated without adjusting either the pump speed or retentate valve for 4.1 hours. The initial and final concentrations were determined to be 25.4±0.6 and 159±6 mg/mL, respectively, by a Bradford assay, as shown in Table 19 below. A caffeine-containing sample was prepared by dissolving 14.2 g of BGG into 566 mL of buffer containing 15 mg/mL caffeine, 150 mM NaCl, and 20 mM histidine, adjusted to pH 6, such that the initial BGG concentration was nominally 25.1 mg/mL. The material was filtered through a 0.2 μm PES filter (VWR, Radnor, Pa.) and then processed in the TFF device. The pump speed and retentate valve were set to identical levels to those previously. The feed and retentate pressures were confirmed to be 30 psi and 10 psi, respectively, as previously. The material was concentrated without adjusting either the pump speed or retentate valve for 4.1 hours. The initial and final concentrations were determined to be 24.4±0.5 and 225±10 mg/mL, respectively, by a Bradford assay, as shown in Table 19 below. The use of caffeine during TFF processing increased the final protein concentration by approximately 42% when compared to the control, from 159 to 225 mg/mL.

TABLE 19

| Sample | Initial concentration (mg/mL) | Final concentration (mg/mL) |
| --- | --- | --- |
| Control | 25.4 ± 0.6 | 159 ± 6 |
| 15 mg/mL caffeine | 24.4 ± 0.5 | 225 ± 10 |

Example 27: Caffeine Effect During Sterile Filtration of BGG Solutions

Bovine gamma globulin (BGG), L-histidine, and caffeine were purchased from Sigma-Aldrich (St. Louis, Mo., product numbers G5009, H6034, and C7731, respectively). Deionized (DI) water was generated from tap water with a Direct-Q 3 UV purification system from EMD Millipore (Billerica, Mass.). 25-mm polyethersulfone (PES) filters with 0.2-µm pores were purchased from GE Healthcare (Chicago, Ill., catalog number 6780-2502). 1-mL Luer-Lok syringes were purchased from Becton, Dickinson and Company (Franklin Lakes, N.J., reference number 309628). A 20-mM histidine buffer, pH 6.0 was prepared using L-histidine, DI water, and titrated to pH 6.0 with 1 M HCl. A 15 mg/mL solution of caffeine was prepared using the histidine buffer. The caffeine-free and caffeine-containing buffers were used to reconstitute BGG to a final concentration of about 280 mg/mL. The protein concentration, c, was calculated using:

$$c = \frac{m_p}{b + vm_p} \quad \text{(Eq. 4)}$$

where $m_p$ is the protein mass, b is the volume of buffer added, and v is the partial specific volume of BGG, here taken to be 0.74 mL/g. The viscosity of each sample was measured using microVisc rheometer (RheoSense, San Ramon, Calif.) at a temperature of 23° C. and shear rate of 250 s$^{-1}$. The energies required to pass the BGG solutions through the sterile filters were measured using a Tensile Compression Tester (TCT, Instron, Needham, Mass., part number 3343) fitted with a 100 N load cell (Instron, Needham, Mass., part number 2519-103). The syringe plungers were depressed at a rate of 159 mm/min for a distance of 50 mm. The energy requirements were calculated by integrating the load-versus-extension curves measured by the TCT, and results are summarized in Table 20 below.

TABLE 20

| Sample | Protein concentration (mg/mL) | Caffeine concentration (mg/mL) | Viscosity (cP) | Energy requirement (mJ) |
|---|---|---|---|---|
| 1 | 280 | 0 | 106 | 198 |
| 2 | 280 | 15.1 | 68.9 | 181 |

Example 28: Excipients to Improve Protein-A Chromatography Elution

Four purified, research-grade biosimilar antibodies, ipilimumab, ustekinumab, omalizumab, and tocilizumab were purchased from Bioceros (Utrecht, The Netherlands). They were provided as frozen aliquots at protein concentrations of 20, 26, 15 and 23 mg/mL, respectively, in an aqueous 40 mM sodium acetate, 50 mM tris-HCl buffer at pH 5.5. The protein solutions were thawed at room temperature prior to measurement and afterwards, were filtered through a 0.2 µm polyethersulfone filters. The filtered protein stock solutions were mixed in 1:1 ratio of protein stock solution to a binding buffer. The binding buffer, used to promote the binding of the antibodies to the Protein-A resin, was composed of 0.1 M sodium phosphate and 0.15 sodium chloride at pH 7.2 in deionized (DI) water. The DI water was produced by purifying tap water with a Direct-Q 3 UV purification system from EMD Millipore (Billerica, Mass.). These solutions were employed to perform Protein-A binding and elution studies using a PIERCE™ Protein-A Spin Plate for IgG Screening (ThermoFisher Scientific catalog #45202). The plate had 96 wells, each containing 50 µL of Protein-A resin. The resin was washed with binding buffer by adding 200 µL of binding buffer to each well and centrifuging the plate at 1000×g for 1 minute and discarding the flow-through. All subsequent centrifugation steps were performed at 1000×g for 1 minute. This wash procedure was repeated once. Following these initial washing steps, the diluted protein samples, i.e., samples containing ipilimumab, ustekinumab, omalizumab, and tocilizumab, were added to the wells in the plate (200 µL per well). The plate was then placed on a Daigger Scientific (Vernon Hills, Ill.) Labgenius orbital shaker and agitated at 260 rpm for 30 minutes, following which the plate was centrifuged and the flow-through was discarded. The wells were then washed by adding 500 µL of binding buffer to each well, centrifuging the plate and discarding the flow-through. This wash step was repeated twice. After these washing steps, the proteins were eluted from the plate using elution buffers to which different excipients had been added. For each elution, 50 µL of a neutralization buffer consisting of 1 M sodium phosphate at pH 7 was added to each well of the collection plate, and then two hundred µL of elution buffer was added to each well of the plate. The plate was agitated at 260 rpm for 1 minute and then centrifuged. The flow-through was recovered for analysis. This elution step was repeated once. The control buffer, with no excipients, contained 20 mM citrate and had a pH of 2.6. Because Protein-A elution buffers often contain some amount of salt, an elution buffer of 100 mM NaCl in the citrate buffer was prepared as a secondary control.

Table 21 lists the excipient solutions used in this example, their concentrations, and final pH of the elution buffers. All excipients were purchased from Sigma Aldrich (St. Louis, Mo.), with the exception of aspartame, which was purchased from Herb Store USA (Los Angeles, Calif.), trehalose, which was purchased from Cascade Analytical Reagents and Biochemicals (Corvallis, Oreg.), and sucrose which was purchased from Research Products International (Mt. Prospect, Ill., product number S24060). All excipient-containing elution buffers were prepared by mixing the appropriate quantity of the excipient with approximately 10 mL of the salt-free citrate buffer control. The elution buffers were prepared at approximately 100 mM excipient. However, not all of the excipients are soluble at this level; Table 21 therefore lists all of the excipient concentrations that were used. The pH of each elution buffer was adjusted to about 2.6±0.1 using either hydrochloride or sodium hydroxide as needed.

For each protein sample, ASD High performance size-exclusion chromatography (SEC) analysis was performed using a TSKgel SuperSW3000 column (30 cm×4.6 mm ID, Tosoh Bioscience, King of Prussia, Pa.) connected to an HPLC workstation (Agilent HP 1100 system). The separation was carried out at a flow of 0.35 mL/min at room temperature. The mobile phase was an aqueous buffer of 100 mM sodium phosphate, 300 mM sodium chloride, pH 7. The protein concentration was monitored by absorbance at 280 nm using an Agilent 1100 Series G1315B diode array detector. The total amount of protein eluted from the Protein-A resin for each protein, i.e., ipilimumab, ustekinumab, omalizumab, and tocilizumab, was estimated by integrating the chromatograms. The integrated peak areas for each protein, i.e., ipilimumab, ustekinumab, omalizumab, and tocilizumab, are listed in Tables 22-25. Tables 22-25 also compare the experimental peak areas to those of the salt-free and salt-containing controls. Values greater than 100% indicate that the elution buffer recovered more protein from the Protein-A resin than the control whereas values less than 100% indicate that the elution buffer recovered less protein from the Protein-A resin than the control.

TABLE 21

Excipients used in Example 28

| Excipient | Sigma-Aldrich product number for excipient | Excipient concentration (mM) | pH |
|---|---|---|---|
| caffeine | C7731 | 79 | 2.6 |
| acesulfame potassium | 04054 | 110 | 2.5 |
| 1-methyl-2-pyrrolidone | M6762 | 117 | 2.6 |
| aspartame | N/A | 20 | 2.6 |
| taurine | T8691 | 114 | 2.5 |
| trehalose | N/A | 100 | 2.7 |
| sucrose | N/A | 101 | 2.7 |
| niacinamide | N5535 | 99 | 2.7 |
| sodium chloride control | S7653 | 117 | 2.6 |
| control | N/A | N/A | 2.5 |

TABLE 22

Ipilimumab recovery from Protein-A resin

| Excipient | Peak area (mAU*min) | Peak area normalized to salt-free control (%) | Peak area normalized to salt control (%) |
|---|---|---|---|
| citrate | 3409 | 77.9 | 83.6 |
| Acesulfame potassium | 1567 | 35.8 | 38.4 |
| 1-methyl-2-pyrrolidone | 386 | 8.8 | 9.5 |
| aspartame | 4012 | 91.7 | 98.3 |
| taurine | 3958 | 90.4 | 97.0 |
| trehalose | 3667 | 83.8 | 89.9 |
| sucrose | 4585 | 104.8 | 112.4 |
| niacinamide | 4295 | 98.2 | 105.3 |
| sodium chloride control | 4080 | 93.2 | 100.0 |
| control | 4376 | 100.0 | 107.2 |

TABLE 23

Ustekinumab recovery from Protein-A resin

| Excipient | Integrated peak area (mAU*min) | Peak area normalized to salt-free control (%) | Peak area normalized to salt control (%) |
|---|---|---|---|
| caffeine | 2301 | 86.6 | 75.2 |
| acesulfame potassium | 307 | 16.2 | 14.0 |
| aspartame | 417 | 17.4 | 15.1 |
| 1-methyl-2-pyrrolidone | 2952 | 108.8 | 94.4 |
| taurine | 3257 | 118.6 | 103.0 |
| trehalose | 1549 | 56.6 | 49.1 |
| sucrose | 1274 | 51.2 | 44.4 |
| niacinamide | 3204 | 116.1 | 100.8 |
| sodium chloride control | 3176 | 115.2 | 100.0 |

TABLE 24

Omalizumab recovery from Protein-A resin

| Excipient | Integrated peak area (mAU*min) | Peak area normalized to salt-free control (%) | Peak area normalized to salt control (%) |
|---|---|---|---|
| caffeine | 4040 | 105.5 | 117.5 |
| acesulfame potassium | 3620 | 94.5 | 105.3 |
| 1-methyl-2-pyrrolidone | 3334 | 87.0 | 97.0 |
| aspartame | 3605 | 94.1 | 104.8 |
| taurine | 4337 | 113.2 | 126.1 |
| trehalose | 3571 | 93.2 | 103.8 |
| sucrose | 3639 | 95.0 | 105.8 |
| niacinamide | 4812 | 125.6 | 139.9 |
| sodium chloride control | 3439 | 89.8 | 100.0 |
| control | 3831 | 100.0 | 111.4 |

TABLE 25

Tocilizumab recovery from Protein-A resin

| Excipient | Integrated peak area (mAU*min) | Peak area normalized to salt-free control (%) | Peak area normalized to salt control (%) |
|---|---|---|---|
| caffeine | 3120 | 111.2 | 100.3 |
| acesulfame potassium | 3083 | 109.9 | 99.1 |
| 1-methyl-2-pyrrolidone | 261 | 9.3 | 8.4 |
| aspartame | 556 | 19.8 | 17.9 |
| taurine | 3054 | 108.8 | 98.2 |
| trehalose | 2781 | 99.1 | 89.4 |
| sucrose | 1037 | 37.0 | 33.3 |
| niacinamide | 2550 | 90.9 | 82.0 |
| sodium chloride control | 3111 | 110.9 | 100.0 |
| control | 2806 | 100.0 | 90.2 |

Example 29: Excipients to Improve Protein-A Chromatography Elution

The test proteins used in this Example are identical to those in Example 28, i.e., ipilimumab, ustekinumab, omalizumab, and tocilizumab. Protein-A binding and elution studies were performed using an identical plate to that in Example 28. The methods for loading and eluting the antibodies from the Protein-A plate were identical to those in Example 28 with the exception of the elution step. In Example 28, two elution washes were performed. However, in this Example, only one wash is performed. As in Example 28, elution buffers were prepared from a 20 mM citrate, pH 2.6 control buffer. The elution buffers are listed in Table 26 below. All of the excipients were purchased from Sigma-Aldrich (St. Louis, Mo.). The recovered protein was analyzed by HPLC in an identical fashion to that in Example 28, and results of protein recovery for each protein, i.e., ipilimumab, ustekinumab, omalizumab, and tocilizumab, are documented in Tables 27-30 below.

TABLE 26

Excipients used in Example 29

| Excipient | Sigma-Aldrich product number | Excipient concentration (mM) | pH |
|---|---|---|---|
| Control | N/A | N/A | 2.5 |
| sodium chloride control | S7653 | 117 | 2.6 |
| niacinamide | N5535 | 99 | 2.7 |
| Taurine | T8691 | 114 | 2.5 |

TABLE 26-continued

Excipients used in Example 29

| Excipient | Sigma-Aldrich product number | Excipient concentration (mM) | pH |
|---|---|---|---|
| imidazole | I5513 | 100 | 2.6 |
| 4-hydroxybenzesulfonic acid | 171506 | 107 | 2.6 |
| Caffeine | C7731 | 79 | 2.6 |

TABLE 27

Ipilimumab recovery from Protein-A resin

| Excipient | Peak area (mAU * min) | Peak area normalized to salt-free control (%) | Peak area normalized to salt control (%) |
|---|---|---|---|
| control | 4841 | 100.0 | 88.3 |
| sodium chloride control | 5485 | 113.3 | 100.0 |
| niacinamide | 6300 | 130.1 | 114.8 |
| taurine | 7557 | 156.1 | 137.8 |
| imidazole | 6071 | 125.4 | 110.7 |
| 4-hydroxybenzesulfonic acid | 5836 | 120.6 | 106.4 |
| caffeine | 6051 | 125.0 | 110.3 |

TABLE 28

Ustekinumab recovery from Protein-A resin

| Excipient | Integrated peak area (mAU * min) | Peak area normalized to salt-free control (%) | Peak area normalized to salt control (%) |
|---|---|---|---|
| control | 4572 | 100.0 | 107.9 |
| sodium chloride control | 4238 | 92.7 | 100.0 |
| niacinamide | 5848 | 127.9 | 138.0 |
| taurine | 4744 | 103.8 | 112.0 |
| imidazole | 4617 | 101.0 | 108.9 |
| 4-hydroxybenzesulfonic acid | 4132 | 90.4 | 97.5 |
| Caffeine | 5084 | 111.2 | 120.0 |

TABLE 29

Omalizumab recovery from Protein-A resin

| Excipient | Integrated peak area (mAU * min) | Peak area normalized to salt-free control (%) | Peak area normalized to salt control (%) |
|---|---|---|---|
| control | 4194 | 100.0 | 91.7 |
| sodium chloride control | 4574 | 109.1 | 100.0 |
| niacinamide | 5748 | 137.0 | 125.7 |
| taurine | 4676 | 111.5 | 102.2 |
| imidazole | 2589 | 61.7 | 56.6 |
| 4-hydroxybenzesulfonic acid | 3190 | 76.1 | 69.7 |
| caffeine | 5807 | 138.5 | 127.0 |

TABLE 30

Tocilizumab recovery from Protein-A resin

| Excipient | Integrated peak area (mAU * min) | Peak area normalized to salt-free control (%) | Peak area normalized to salt control (%) |
|---|---|---|---|
| control | 4667 | 100.0 | 97.5 |
| sodium chloride control | 4786 | 102.6 | 100.0 |
| niacinamide | 5225 | 111.9 | 109.2 |
| taurine | 5396 | 115.6 | 112.7 |
| imidazole | 4754 | 101.9 | 99.3 |
| 4-hydroxybenzesulfonic acid | 4539 | 97.3 | 94.8 |
| caffeine | 5656 | 121.2 | 118.2 |

Example 30: Excipients that Improve Omalizumab Elution from Protein-A Chromatography Column Research-grade omalizumab was purchased from Bioceros (Utrecht, The Netherlands) and provided frozen at 15 mg/mL in an aqueous 40 mM sodium acetate, 50 mM tris-HCl buffer, pH 5.5. The protein was thawed at room temperature prior to experiments and filtered through a 0.2 µm polyethersulfone filter. The filtered material was mixed in a 1:1 ratio with a binding buffer that consisted of 20 mM sodium phosphate, pH 7 in DI water. Tap water was purified with a Direct-Q 3 UV purification system from EMD Millipore (Billerica, Mass.) to produce the DI water. Protein-A purification was performed using a HiTrap Protein-A HP 1 mL column from GE Healthcare (Chicago, Ill., product number 29048576). For each experiment, the column was first equilibrated with 10 mL of binding buffer. Following equilibration, 30 mg of protein were loaded onto the Protein-A column. The column was then washed with 5 mL of binding buffer. After washing the column, bound omalizumab was eluted from the column using fractions of one of the elution buffers listed in Table 31 below. The elution buffers were prepared by dissolving the indicated excipients in a 20 mM citrate buffer, pH 4.0. All elution buffers were adjusted to pH 4.0. Five 1-mL fractions were collected. Finally, Protein-A was regenerated by washing the column with 5 mL of 100 mM citrate, pH 3.0 buffer. The flowrate for each step was 1 mL/min, which was maintained by a Fusion 100 infusion pump (Chemyx, Stafford, Tex.). 10-mL NormJect Luer Lok syringes were used (Henke Sass Wolf, Tuttlingen, Germany, reference number 4100-000V0).

Elution fractions, E1, E2, E3, E4, and E5, were assayed for total protein content by high performance size-exclusion chromatography (SEC) analysis. SEC analysis was performed using a TSKgel SuperSW3000 column (30 cm×4.6 mm ID, Tosoh Bioscience, King of Prussia, Pa.) connected to an HPLC workstation (Agilent HP 1100 system). The separation was carried out at a flow of 0.35 mL/min at room temperature. The mobile phase was an aqueous buffer of 100 mM sodium phosphate, 300 mM sodium chloride, pH 7. The protein concentration was monitored by absorbance at 280 nm using an Agilent 1100 Series G1315B diode array detector. The total amount of protein eluted from the Protein-A resin was estimated by integrating the chromatograms.

Citrate is a common excipient used in Protein-A chromatography and was therefore used here as a control. The eluate fractions for the control sample exhibited insoluble aggregates on storage overnight at 4° C. as evidenced by the formation of a precipitate phase. Therefore, the peak areas reported in Table 31 below represent the total soluble protein amounts in the eluate fractions. We note that insoluble aggregates were only observed in the control sample and none of the other samples exhibited such aggregates. Peak areas greater than that of the control (using the citrate excipient) indicate that the use of the test excipient can enable a more efficient separation of protein from the column.

TABLE 31

Omalizumab elution from Protein-A column

| Elution excipient | Elution excipient concentration (mM) | E1 peak area (mAU*min) | E2 peak area (mAU*min) | E3 peak area (mAU*min) | E4 peak area (mAU*min) | E5 peak area (mAU*min) | Total peak area (mAU*min) |
|---|---|---|---|---|---|---|---|
| citrate (control) | 103 | 352 | 9670 | 4098 | 4245 | 2953 | 21318 |
| imidazole | 100 | 236 | 10224 | 7373 | 3894 | 2620 | 24348 |
| taurine | 125 | 408 | 17018 | 7676 | 3349 | 2211 | 30662 |
| niacinamide | 102 | 228 | 14492 | 5307 | 2914 | 2014 | 24955 |
| caffeine | 81 | 617 | 21965 | 8069 | 3301 | 1911 | 35863 |

Example 31: Formulations of BGG with Different Amounts of Caffeine Excipient Formulations were prepared with different molar concentrations of caffeine (at concentrations listed in Table 32 below) and a test protein, where the test protein was intended to simulate a therapeutic protein that would be used in a therapeutic formulation. The formulations for this Example were prepared in 20 mM histidine buffer for viscosity measurement in the following way. Stock solutions of 0 and 80 mM caffeine were prepared in 20 mM histidine and the resulting solution pH adjusted with small amounts of sodium hydroxide or hydrochloric acid to achieve pH 6 prior to dissolution of the model protein. Additional solutions at various caffeine concentrations were prepared by blending the two stock solutions at various volume ratios, to provide a series of caffeine-containing solutions, at concentrations listed in Table 32 below. Once these excipient solutions had been prepared, the test protein bovine gamma globulin (BGG) was dissolved into each test solution at a ratio to achieve a final protein concentration of about 280 mg/mL by adding 0.7 mL of each excipient solution to 0.25 g lyophilized BGG powder. The BGG-containing solutions were formulated in 5 mL sterile polypropylene tubes and allowed to shake at 100 rpm on an orbital shaker table overnight. These solutions were then transferred to 2 mL microcentrifuge tubes and centrifuged for about five minutes at 2400 rpm in an IEC MicroMax microcentrifuge to remove entrained air prior to viscosity measurement.

Viscosity measurements of formulations prepared as described above were made with a microVisc viscometer (RheoSense, San Ramon, Calif.). The viscometer was equipped with an A-10 chip having a channel depth of 100 microns, and was operated at a shear rate of 250 l/s and 25° C. To measure viscosity, the test formulation was loaded into the viscometer, taking care to remove all air bubbles from the pipet. The pipet containing the loaded sample formulation was placed in the instrument and allowed to incubate at the measurement temperature for about five minutes. The instrument was then run until the channel was fully equilibrated with the test fluid, indicated by a stable viscosity reading, and then the viscosity recorded in centipoise. Viscosity results that were obtained are presented in Table 32 below.

TABLE 32

| Caffeine conc (mM) | Viscosity (cP) | Normalized Viscosity |
|---|---|---|
| 0 | 83 | 1.00 |
| 5 | 67 | 0.81 |
| 10 | 70 | 0.84 |
| 20 | 77 | 0.92 |
| 30 | 63 | 0.76 |
| 40 | 65 | 0.78 |
| 50 | 65 | 0.78 |
| 60 | 57 | 0.69 |
| 70 | 50 | 0.60 |
| 80 | 50 | 0.60 |

Example 32: Preparation of Solutions of Co-Solutes in Deionized Water

Compounds used as co-solutes to increase caffeine solubility in water were obtained from Sigma-Aldrich (St. Louis, Mo.) and included niacinamide, proline, procaine HCl, ascorbic acid, 2,5-dihydroxybenzoic acid, lidocaine, saccharin, acesulfame K, tyramine, and aminobenzoic acid. Solutions of each co-solute were prepared by dissolving dry solid in deionized water and in some cases adjusting the pH to a value between pH of about 6 and pH of about 8 with 5 M hydrochloric acid or 5 M sodium hydroxide as necessary. Solutions were then diluted to a final volume of either 25 mL or 50 mL using a Class A volumetric flask and concentration recorded based on the mass of compound dissolved and the final volume of the solution. Prepared solutions were used either neat or diluted with deionized water.

Example 33: Caffeine Solubility Testing

The impact of different co-solutes on the solubility of caffeine at ambient temperature (about 23° C.) was assessed in the following way. Dry caffeine powder (Sigma-Aldrich, St. Louis, Mo.) was added to 20 mL glass scintillation vials and the mass of caffeine recorded. 10 mL of a co-solute solution prepared in accordance with Example 32 was added to the caffeine powder in certain cases; in other cases, a blend of a co-solute solution and deionized water was added to the caffeine powder, maintaining a final addition volume of 10 mL. The volume contribution of the dry caffeine powder was assumed to be negligible in any of these mixtures. A small magnetic stir bar was added to the vial, and the solution was allowed to mix vigorously on a stir plate for about 10 minutes. After about 10 minutes the vial was observed for dissolution of the dry caffeine powder, and the results are given in Table 33 below. These observations indicated that niacinamide, procaine HCl, 2,5-dihydroxybenzoic acid sodium salt, saccharin sodium salt, and tyramine chloride salt all enabled dissolution of caffeine to at least about four times the reported caffeine solubility limit (~16 mg/mL at room temperature according to Sigma-Aldrich).

TABLE 33

| Test No. | Co-solute Name | Conc. (mg/mL) | Caffeine (mg/mL) | Observation |
|---|---|---|---|---|
| 33.1 | Proline | 100 | 50 | DND |
| 33.2 | Niacinamide | 100 | 50 | CD |
| 33.3 | Niacinamide | 100 | 60 | CD |
| 33.4 | Niacinamide | 100 | 75 | CD |
| 33.5 | Niacinamide | 100 | 85 | CD |
| 33.6 | Niacinamide | 100 | 100 | CD |
| 33.7 | Niacinamide | 80 | 85 | CD |
| 33.8 | Niacinamide | 50 | 80 | CD |
| 33.9 | Procaine HCl | 100 | 85 | CD |
| 33.10 | Procaine HCl | 50 | 80 | CD |
| 33.11 | Niacinamide | 30 | 80 | DND |
| 33.12 | Procaine HCl | 30 | 80 | DND |
| 33.13 | Niacinamide | 40 | 80 | MD |
| 33.14 | Procaine HCl | 40 | 80 | DND |
| 33.15 | Ascorbic acid, Na | 50 | 80 | DND |
| 33.16 | Ascorbic acid, Na | 100 | 80 | DND |
| 33.17 | 2,5 DHBA, Na | 40 | 80 | CD |
| 33.18 | 2,5 DHBA, Na | 20 | 80 | MD |
| 33.19 | Lidocaine HCl | 40 | 80 | DND |
| 33.20 | Saccharin, Na | 90 | 80 | CD |
| 33.21 | Acesulfame K | 80 | 80 | DND |
| 33.22 | Tyramine HCl | 60 | 80 | CD |
| 33.23 | Na Aminobenzoate | 46 | 80 | DND |
| 33.24 | Saccharin, Na | 45 | 80 | DND |
| 33.25 | Tyramine HCl | 30 | 80 | DND |

CD = completely dissolved;
MD = mostly dissolved;
DND = did not dissolve

Example 34: Profile of HUMIRA®

HUMIRA® (AbbVie Inc., Chicago, Ill.) is a commercially available formulation of the therapeutic monoclonal antibody adalimumab, a TNF-alpha blocker typically prescribed to reduce inflammatory responses of autoimmune diseases such as rheumatoid arthritis, psoriatic arthritis, ankylosing spondylitis, Crohn's disease, ulcerative colitis, moderate to severe chronic psoriasis and juvenile idiopathic arthritis. HUMIRA® is sold in 0.8 mL single use doses containing 40 mg of adalimumab, 4.93 mg sodium chloride, 0.69 mg sodium phosphate monobasic dihydrate, 1.22 mg sodium phosphate dibasic dihydrate, 0.24 mg sodium citrate, 1.04 mg citric acid monohydrate, 9.6 mg mannitol and 0.8 mg polysorbate 80. A viscosity vs. concentration profile of this formulation was generated in the following way. An Amicon Ultra 15 centrifugal concentrator with a 30 kDa molecular weight cut-off (EMD-Millipore, Billerica, Mass.) was filled with about 15 mL of deionized water and centrifuged in a Sorvall Legend RT (ThermoFisher Scientific) at 4000 rpm for 10 minutes to rinse the membrane. Afterwards the residual water was removed and 2.4 mL of HUIMIRA® liquid formulation was added to the concentrator tube and was centrifuged at 4000 rpm for 60 minutes at 25° C. Concentration of the retentate was determined by diluting 10 microliters of retentate with 1990 microliters of deionized water, measuring absorbance of the diluted sample at 280 nm, and calculating the concentration using the dilution factor and extinction coefficient of 1.39 mL/mg-cm. Viscosity of the concentrated sample was measured with a microVisc viscometer equipped with an A05 chip (RheoSense, San Ramon, Calif.) at a shear rate of 250 sec$^{-1}$ at 23° C. After viscosity measurement, the sample was diluted with a small amount of filtrate and concentration and viscosity measurements were repeated. This process was used to generate viscosity values at varying adalimumab concentrations, as set forth in Table 34 below.

TABLE 34

| Adalimumab concentration (mg/mL) | Viscosity (cP) |
|---|---|
| 277 | 125 |
| 253 | 63 |
| 223 | 34 |
| 202 | 20 |
| 182 | 13 |

Example 35: Reformulation of HUMIRA® with Viscosity-Reducing Excipient

The following example describes a general process by which HUMIRA® was reformulated in buffer with viscosity-reducing excipient. A solution of the viscosity-reducing excipient was prepared in 20 mM histidine by dissolving about 0.15 g histidine and 0.75 g caffeine (Sigma-Aldrich, St. Louis, Mo.) in deionized water. The pH of the resulting solution was adjusted to about 5 with 5 M hydrochloric acid. The solution was then diluted to a final volume of 50 mL in a volumetric flask with deionized water. The resulting buffered viscosity-reducing excipient solution was then used to reformulate HUMIRA® at high mAb concentrations. Next, about 0.8 mL of HUMIRA® was added to a rinsed Amicon Ultra 15 centrifugal concentrator tube with a 30 kDa molecular weight cutoff and centrifuged in a Sorvall Legend RT at 4000 rpm and 25° C. for 8-10 minutes. Afterwards about 14 mL of the buffered viscosity-reducing excipient solution prepared as described above was added to the concentrated HUMIRA® in the centrifugal concentrator. After gentle mixing, the sample was centrifuged at 4000 rpm and 25° C. for about 40-60 minutes. The retentate was a concentrated sample of HUIMIRA® reformulated in a buffer with viscosity-reducing excipient. Viscosity and concentration of the sample were measured, and in some cases then diluted with a small amount of filtrate to measure viscosity at a lower concentration. Viscosity measurements were completed with a microVisc viscometer in the same way as with the concentrated HUMIRA® formulation in the previous example. Concentrations were determined with a Bradford assay using a standard curve generated from HUMIRA® stock solution diluted in deionized water. Reformulation of HUMIRA® with the viscosity-reducing excipient gave viscosity reductions of 30% to 60% compared to the viscosity values of HUMIRA® concentrated in the commercial buffer without reformulation, as set forth in Table 35 below.

TABLE 35

| Adalimumab concentration (mg/mL) | Viscosity (cP) |
|---|---|
| 290 | 61 |
| 273 | 48 |
| 244 | 20 |
| 205 | 14 |

Example 36: Improved Stability of Adalimumab Solutions with Caffeine as Excipient The stability of adalimumab solutions with and without caffeine excipient was evaluated after exposing samples to 2 different stress conditions: agitation and freeze-thaw. The adalimumab drug formulation HUMIRA® (AbbVie) was used, having properties described in more detail in Example 34. The HUMIRA® sample was concentrated to 200 mg/mL adalimumab concentration in the original buffer solution as described in Example 39; this concentrated sample is designated "Sample 1." A second sample was prepared with ~200 mg/mL of adalimumab and 15 mg/mL of added caffeine as described in Example 40; this concentrated sample with added caffeine is designated "Sample 2." Both samples were diluted to a final concentration of 1 mg/mL adalimumab with the diluents as follows: Sample 1 diluent is the original buffer solution, and Sample 2 diluent is a 20 mM histidine, 15 mg/mL caffeine, pH=5. Both HUMIRA® dilutions were filtered through a 0.22 μm syringe filter. For every diluted sample, 3 batches of 300 μL each were prepared in a 2 mL Eppendorf tube in a laminar flow hood. The samples were submitted to the following stress conditions: for agitation, samples were placed in an orbital shaker at 300 rpm for 91 hours; for freeze-thaw, samples were cycled 7 times from −17 to 30° C. for an average of 6 hours per condition. Table 36 describes the samples prepared.

TABLE 36

| Sample # | Excipient added | Stress condition |
|---|---|---|
| 1-C | None | None |
| 1-A | None | Agitation |
| 1-FT | None | Freeze-Thaw |
| 2-C | 15 mg/mL caffeine | None |
| 2-A | 15 mg/mL caffeine | Agitation |
| 2-FT | 15 mg/mL caffeine | Freeze-Thaw |

Example 37: Evaluation of Stability by Dynamic Light Scattering (DLS)

A Brookhaven Zeta Plus dynamic light scattering instrument was used to measure the hydrodynamic radius of the adalimumab molecules in the samples from Example 36, and to look for evidence of the formation of aggregate populations. Table 37 shows the DLS results for the 6 samples prepared according to Example 36: some of them (1-A, 1-FT, 2-A, and 2-FT) had been exposed to stress conditions ("Stressed Samples"), and others (1-C and 2-C) had not been stressed. The DLS data in Table 37 show a multimodal particle size distribution of the monoclonal antibody in Stressed Samples that do not contain caffeine. In the absence of caffeine as an excipient, the Stressed Samples 1-A and 1-FT showed higher effective diameter than non-stressed Sample 1-C, and in addition they showed a second population of particles of significantly higher diameter; this new grouping of particles with a larger diameter is evidence of aggregation into subvisible particles. The Stressed Samples containing the caffeine (Samples 2-A and 2-FT) only display one population of particles, at a particle diameter similar to the unstressed Sample 2-C. These results demonstrate that adding caffeine to these samples reduced the formation of aggregates or subvisible particles.

TABLE 37

| Sample # | Effective Diameter (nm) | Diameter of Population #1 (nm) | % by Intensity of Population #1 | Diameter of Population #2 (nm) | % by Intensity of Population #2 |
|---|---|---|---|---|---|
| 1-C | 10.9 | 10.8 | 100 | — | — |
| 1-A | 11.5 | 10.8 | 87 | 28.9 | 13 |
| 1-FT | 20.4 | 11.5 | 66 | 112.2 | 44 |
| 2-C | 10.5 | 10.5 | 100 | — | — |
| 2-A | 10.8 | 10.8 | 100 | — | — |
| 2-FT | 11.4 | 11.4 | 100 | — | — |

Tables 38A and Table 38B display the DLS raw data of adalimumab samples from Example 36 showing the particle size distributions. In these Tables, G(d) is the intensity-weighted differential size distribution. C(d) is the cumulative intensity-weighted differential size distribution.

TABLE 38A

| Sample 1-C | | | Sample 1-A | | | Sample 1-FT | | |
|---|---|---|---|---|---|---|---|---|
| Diameter (nm) | G (d) | C(d) | Diameter (nm) | G (d) | C(d) | Diameter (nm) | G (d) | C(d) |
| 10.6 | 14 | 4 | 9.3 | 13 | 3 | 8.2 | 12 | 2 |
| 10.6 | 53 | 20 | 9.8 | 47 | 15 | 9.2 | 55 | 13 |
| 10.7 | 92 | 46 | 10.3 | 87 | 37 | 10.3 | 98 | 32 |
| 10.8 | 100 | 76 | 10.8 | 100 | 63 | 11.5 | 100 | 52 |
| 10.9 | 61 | 93 | 11.4 | 67 | 80 | 12.9 | 57 | 63 |
| 10.9 | 22 | 100 | 12 | 27 | 87 | 14.5 | 14 | 66 |
| | | | 26.1 | 4 | 88 | 89.3 | 5 | 67 |
| | | | 27.5 | 10 | 91 | 100.1 | 27 | 72 |
| | | | 28.9 | 13 | 94 | 112.2 | 52 | 83 |
| | | | 30.5 | 13 | 97 | 125.7 | 52 | 93 |
| | | | 32.1 | 7 | 99 | 140.8 | 30 | 99 |
| | | | 33.8 | 4 | 100 | 157.8 | 7 | 100 |

TABLE 38B

| Sample 2-C | | | Sample 2-A | | | Sample 2-FT | | |
|---|---|---|---|---|---|---|---|---|
| Diameter (nm) | G (d) | C(d) | Diameter (nm) | G (d) | C(d) | Diameter (nm) | G (d) | C(d) |
| 10.3 | 14 | 4 | 10.6 | 7 | 2 | 11.3 | 28 | 9 |
| 10.4 | 52 | 19 | 10.6 | 43 | 16 | 11.3 | 64 | 29 |
| 10.5 | 91 | 46 | 10.7 | 79 | 40 | 11.4 | 100 | 60 |
| 10.5 | 100 | 75 | 10.8 | 100 | 71 | 11.5 | 79 | 85 |
| 10.6 | 62 | 93 | 10.8 | 64 | 91 | 11.5 | 43 | 98 |
| 10.7 | 23 | 100 | 10.9 | 29 | 100 | 11.6 | 7 | 100 |

Example 38: Evaluation of Stability by Size-Exclusion Chromatography (SEC)

Size exclusion chromatography was used to detect subvisible particulates of less than about 0.1 microns in size from the stressed and unstressed adalimumab samples described in Example 36. To perform the SEC, a TSKgel SuperSW3000 column (Tosoh Biosciences, Montgomeryville, Pa.) with a guard column was used, and the elution was monitored at 280 nm. A total of 10 μL of each stressed and unstressed sample from Example 36 was eluted isocratically with a pH 6.2 buffer (100 mM phosphate, 325 mM NaCl), at a flow rate of 0.35 mL/min. The retention time of the adalimumab monomer was approximately 9 minutes. No detectable aggregates were identified in the samples containing the caffeine excipient, and the amount of monomer in all 3 samples remained constant.

Example 39: Viscosity Reduction of HERCEPTIN® Formulation

The monoclonal antibody trastuzumab (HERCEPTIN® from Genentech) was received as a lyophilized powder and reconstituted to 21 mg/mL in DI water. The resulting solution was concentrated as-is in an Amicon Ultra 4 centrifugal concentrator tube (molecular weight cut-off, 30 kDa) by centrifuging at 3500 rpm for 1.5 hrs. The concentration was measured by diluting the sample 200 times in an appropriate buffer and measuring absorbance at 280 nm using the extinction coefficient of 1.48 mL/mg. Viscosity was measured using a RheoSense microVisc viscometer.

Excipient buffers were prepared containing salicylic acid and caffeine either alone or in combination by dissolving histidine and excipients in distilled water, then adjusting pH to the appropriate level. The conditions of Buffer Systems 1 and 2 are summarized in Table 39.

TABLE 39

| Buffer System # | Salicylic Acid concentration | Caffeine concentration | Osmolality (mOsm/kg) | pH |
|---|---|---|---|---|
| 1 | 10 mg/mL | 10 mg/mL | 145 | 6 |
| 2 | 0 | 15 mg/mL | 86 | 6 |

HERCEPTIN® solutions were diluted in the excipient buffers at a ratio of ~1:10 and concentrated in Amicon Ultra 15 (MWCO 30 kDa) concentrator tubes. Concentration was determined using a Bradford assay and compared with a standard calibration curve made from the stock HERCEPTIN® sample. Viscosity was measured using the RheoSense microVisc viscometer. The concentration and viscosity measurements of the various HERCEPTIN® solutions are shown in Table 40 below, where Buffer Systems 1 and 2 refer to those buffers described in Table 39.

TABLE 40

| Control solution with no added excipients | | Buffer System 1: Solution with 10 mg/mL Caffeine + 10 mg/ml Salicylic Acid added | | Buffer System 2: Solution with 15 mg/mL Caffeine added | |
|---|---|---|---|---|---|
| Viscosity (cP) | Antibody Concentration (mg/mL) | Viscosity (cP) | Concentration (mg/mL) | Viscosity (cP) | Antibody Concentration (mg/mL) |
| 37.2 | 215 | 9.7 | 244 | 23.4 | 236 |
| 9.3 | 161 | 7.7 | 167 | 12.2 | 200 |
| 3.1 | 108 | 2.9 | 122 | 5.1 | 134 |
| 1.6 | 54 | 2.4 | 77 | 2.1 | 101 |

Buffer System 1, containing both salicylic acid and caffeine, had a maximum viscosity reduction of 76% at 215 mg/mL compared to the control sample. Buffer System 2, containing just caffeine, had viscosity reduction up to 59% at 200 mg/mL.

Example 40: Viscosity Reduction of AVASTIN® Formulation

AVASTIN® (monoclonal antibody bevacizumab formulation marketed by Genentech) was received as a 25 mg/mL solution in a histidine buffer. The sample was concentrated in Amicon Ultra 4 centrifugal concentrator tubes (MWCO 30 kDa) at 3500 rpm. Viscosity was measured by RheoSense microVisc and concentration was determined by absorbance at 280 nm (extinction coefficient, 1.605 mL/mg). The excipient buffer was prepared by adding 10 mg/mL caffeine along with 25 mM histidine HCl. AVASTIN® stock solution was diluted with the excipient buffer then concentrated in Amicon Ultra 15 centrifugal concentrator tubes (MWCO 30 kDa). The concentration of the excipient samples was determined by Bradford assay and the viscosity was measured using the RheoSense microVisc. Results are shown in Table 41 below.

TABLE 41

| Concentration (mg/mL) | Viscosity without added excipient (cP) | Viscosity with 10 mg/mL added caffeine excipient (cP) | % Viscosity Reduction from Excipient |
|---|---|---|---|
| 266 | 297 | 113 | 62% |
| 213 | 80 | 22 | 73% |
| 190 | 21 | 13 | 36% |

AVASTIN® showed a maximum viscosity reduction of 73% when concentrated with 10 mg/mL of caffeine to 213 mg/mL when compared to the control AVASTIN® sample.

Example 41: Preparation of Formulations Containing Caffeine, a Secondary Excipient and Test Protein Formulations were prepared using caffeine as the excipient compound or a combination of caffeine and a second excipient compound, and a test protein, where the test protein was intended to simulate a therapeutic protein that would be used in a therapeutic formulation. Such formulations were prepared in 20 mM histidine buffer with different excipient compounds for viscosity measurement in the following way. Excipient combinations (Excipients A and B, as described in Table 28 below) were dissolved in 20 mM histidine and the resulting solution pH adjusted with small amounts of sodium hydroxide or hydrochloric acid to achieve pH 6 prior to dissolution of the model protein. Once excipient solutions had been prepared, the test protein bovine gamma globulin (BGG) was dissolved at a ratio to achieve a final protein concentration of about 280 mg/mL. Solutions of BGG in the excipient solutions were formulated in 20 mL glass scintillation vials and allowed to shake at 80-100 rpm on an orbital shaker table overnight. BGG solutions were then transferred to 2 mL microcentrifuge tubes and centrifuged for about ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample in Table 42 below. Viscosities of solutions with excipient were normalized to the viscosity of the model protein solution without excipient. The normalized viscosity is the ratio of the viscosity of the model protein solution with excipient to the viscosity of the model protein solution with no excipient.

TABLE 42

| Excipient A | | Excipient B | | Normalized |
|---|---|---|---|---|
| Name | Conc. (mg/mL) | Name | Conc. (mg/mL) | Viscosity |
| — | 0 | — | 0 | 1.00 |
| Caffeine | 15 | — | 0 | 0.77 |
| Caffeine | 15 | Sodium acetate | 12 | 0.77 |
| Caffeine | 15 | Sodium sulfate | 14 | 0.78 |
| Caffeine | 15 | Aspartic acid | 20 | 0.73 |
| Caffeine | 15 | $CaCl_2$ dihydrate | 15 | 0.65 |
| Caffeine | 15 | Dimethyl Sulfone | 25 | 0.65 |
| Caffeine | 15 | Arginine | 20 | 0.63 |
| Caffeine | 15 | Leucine | 20 | 0.69 |
| Caffeine | 15 | Phenylalanine | 20 | 0.60 |
| Caffeine | 15 | Niacinamide | 15 | 0.63 |
| Caffeine | 15 | Ethanol | 22 | 0.65 |

Example 42: Preparation of Formulations Containing Dimethyl Sulfone and Test Protein Formulations were prepared using dimethyl sulfone (Jarrow Formulas, Los Angeles, Calif.) as the excipient compound and a test protein, where the test protein was intended to simulate a therapeutic protein that would be used in a therapeutic formulation. Such formulations were prepared in 20 mM histidine buffer for viscosity measurement in the following way. Dimethyl sulfone was dissolved in 20 mM histidine and the resulting solution pH adjusted with small amounts of sodium hydroxide or hydrochloric acid to achieve pH 6 and then filtered through a 0.22 micron filter prior to dissolution of the model protein. Once excipient solutions had been prepared, the test protein bovine gamma globulin (BGG) was dissolved at a concentration of about 280 mg/mL. Solutions of BGG in the excipient solutions were formulated in 20 mL glass scintillation vials and allowed to shake at 80-100 rpm on an orbital shaker table overnight. BGG solutions were then transferred to 2 mL microcentrifuge tubes and centrifuged for about ten minutes at 2300 rpm in an IEC MicroMax microcentrifuge to remove entrained air prior to viscosity measurement.

Viscosity measurements of formulations prepared as described above were made with a DV-IIT LV cone and plate viscometer (Brookfield Engineering, Middleboro, Mass.). The viscometer was equipped with a CP-40 cone and was operated at 3 rpm and 25° C. The formulation was loaded into the viscometer at a volume of 0.5 mL and allowed to incubate at the given shear rate and temperature for 3 minutes, followed by a measurement collection period of twenty seconds. This was then followed by 2 additional steps consisting of 1 minute of shear incubation and subsequent twenty second measurement collection period. The three data points collected were then averaged and recorded as the viscosity for the sample. Viscosities of solutions with excipient were normalized to the viscosity of the model protein solution without excipient. The normalized viscosity recorded in Table 43 is the ratio of the viscosity of the model protein solution with excipient to the viscosity of the model protein solution with no excipient.

TABLE 43

| Dimethyl sulfone concentration (mg/mL) | Normalized viscosity |
|---|---|
| 0 | 1.00 |
| 15 | 0.92 |
| 30 | 0.71 |
| 50 | 0.71 |
| 30 | 0.72 |

EQUIVALENTS

While specific embodiments of the subject invention have been disclosed herein, the above specification is illustrative and not restrictive. While this invention has been particularly shown and described with references to preferred embodiments thereof, it will be understood by those skilled in the art that various changes in form and details may be made therein without departing from the scope of the invention encompassed by the appended claims. Many variations of the invention will become apparent to those of skilled art upon review of this specification. Unless otherwise indicated, all numbers expressing reaction conditions, quantities of ingredients, and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

What is claimed is:

1. A method of improving a parameter of a filtration process, wherein the filtration process is the filtration of a protein solution, the method comprising:
   preparing a caffeine-containing protein solution by adding a viscosity-reducing amount of caffeine to a carrier solution, and adding the protein to the carrier solution before or after the addition of the caffeine, and
   filtering the caffeine-containing protein solution;
   wherein the improved parameter is selected from the group consisting of:
   i. a faster filtration rate than the filtration rate of a control solution;
   ii. production of a lower amount of aggregated protein than the amount of aggregated protein produced by a control filtration process;
   iii. a higher mass transfer efficiency than the mass transfer efficiency of the control filtration process; and iv. a higher concentration or a higher yield of the protein than the concentration or yield of the protein produced by the control filtration process;

wherein the control solution does not contain caffeine but is otherwise identical to the caffeine-containing protein solution, and wherein the control filtration process is identical to the filtration of the caffeine-containing solution except that it is performed with the control solution instead of the caffeine-containing protein solution.

2. The method of claim 1, wherein the filtration process is a virus removal filtration process or an ultrafiltration/diafiltration process.

3. The method of claim 1, wherein the improved parameter is the faster filtration rate than the filtration rate of the control solution.

4. The method of claim 1, wherein the improved parameter is the production of a smaller amount of aggregated protein than the amount of aggregated protein produced by the control filtration process.

5. The method of claim 1, wherein the improved filtration-related parameter is the higher mass transfer efficiency than the mass transfer efficiency of the control filtration process.

6. The method of claim 1, wherein the improved parameter is the higher concentration or the higher yield of the protein than the concentration or yield of the protein produced by the control filtration process.

7. The method of claim 1, wherein the viscosity-reducing amount is between about 1 mg/mL to about 22 mg/mL of the caffeine.

8. The method of claim 1, wherein the carrier solution comprises an additional agent selected from the group consisting of preservatives, sugars, polysaccharides, arginine, proline, surfactants, stabilizers, and buffers.

9. The method of claim 1, wherein the protein is a therapeutic protein.

10. The method of claim 9, wherein the therapeutic protein is selected from the group consisting of a monoclonal antibody, a polyclonal antibody, an antibody fragment, a fusion protein, a PEGylated protein, an antibody-drug conjugate, a synthetic polypeptide, a protein fragment, a lipoprotein, an enzyme, and a structural peptide.

11. The method of claim 9, wherein the therapeutic protein is a recombinant protein.

12. The method of claim 1, further comprising a step of adding a second viscosity-reducing excipient to the carrier solution.

13. The method of claim 1, wherein the viscosity-reducing amount is 30 mg/ml or less.

14. The method of claim 1, wherein the viscosity-reducing amount is 22 mg/ml or less.

15. The method of claim 1, wherein the viscosity-reducing amount is 15 mg/ml or less.

16. The method of claim 1, wherein the filtration process is tangential flow filtration (TFF).

17. The method of claim 1, wherein the filtration process is sterile filtration.

18. The method of claim 2, wherein the filtration process is a virus removal filtration process.

19. The method of claim 18, wherein the virus removal filtration process is nanofiltration.

20. The method of claim 2, wherein the filtration process is an ultrafiltration/diafiltration process.

21. The method of claim 12, wherein the second viscosity-reducing excipient is theophylline, tyramine, procaine, lidocaine, imidazole, aspartame, saccharin, and acesulfame potassium, niacinamide, and isonicotinamide.

* * * * *